(12) United States Patent
Subkowski et al.

(10) Patent No.: US 7,910,699 B2
(45) Date of Patent: *Mar. 22, 2011

(54) CYSTEINE-DEPLETED HYDROPHOBIN FUSION PROTEINS, THEIR PRODUCTION AND USE THEREOF

(75) Inventors: Thomas Subkowski, Ladenburg (DE); Marvin Karos, Schwetzingen (DE); Hans-Georg Lemaire, Limburgerhof (DE); Heiko Barg, Speyer (DE); Claus Bollschweiler, Heidelberg (DE)

(73) Assignee: BASF SE (DE)

(*) Notice: Subject to any disclaimer, the term of this patent is extended or adjusted under 35 U.S.C. 154(b) by 23 days.

This patent is subject to a terminal disclaimer.

(21) Appl. No.: 11/921,905

(22) PCT Filed: Jun. 9, 2006

(86) PCT No.: PCT/EP2006/063066
§ 371 (c)(1),
(2), (4) Date: Dec. 10, 2007

(87) PCT Pub. No.: WO2006/131564
PCT Pub. Date: Dec. 14, 2006

(65) Prior Publication Data
US 2009/0136996 A1   May 28, 2009

(30) Foreign Application Priority Data

Jun. 10, 2005   (DE) .................. 10 2005 027 139

(51) Int. Cl.
*C07K 14/00*   (2006.01)
(52) U.S. Cl. ........................................ 530/350
(58) Field of Classification Search ............... None
See application file for complete search history.

(56) References Cited

U.S. PATENT DOCUMENTS

| | | | |
|---|---|---|---|
| 2,399,161 A | 4/1946 | Brother et al. | |
| 3,751,280 A | 8/1973 | Nerurkar et al. | |
| 4,129,706 A | 12/1978 | Keppler et al. | |
| 4,241,191 A | 12/1980 | Keppler et al. | |
| 5,015,677 A | 5/1991 | Benedict et al. | |
| 5,049,504 A | 9/1991 | Maugh et al. | |
| 5,110,835 A | 5/1992 | Walter et al. | |
| 5,290,819 A | 3/1994 | Witt et al. | |
| 5,859,198 A | 1/1999 | Haber | |
| 6,977,239 B1 | 12/2005 | Weuthen et al. | |
| 7,241,734 B2 * | 7/2007 | Sweigard et al. | 514/2 |
| 2003/0049726 A1 | 3/2003 | Holloway et al. | |
| 2003/0113454 A1 | 6/2003 | de Vocht et al. | |
| 2003/0134042 A1 | 7/2003 | de Vocht et al. | |
| 2003/0217419 A1 | 11/2003 | Vic | |
| 2006/0040349 A1 | 2/2006 | Sweigard et al. | |
| 2007/0077619 A1 | 4/2007 | Ostermann et al. | |

FOREIGN PATENT DOCUMENTS

| | | |
|---|---|---|
| DE | 2638839 A1 | 3/1976 |
| DE | 2609104 A1 | 9/1977 |
| DE | 4220225 A1 | 12/1993 |
| DE | 19942539 A1 | 3/2001 |
| DE | 10200402580 A1 | 12/2005 |
| EP | 0252561 A2 | 1/1988 |
| EP | 0470455 A2 | 2/1992 |
| EP | 0611824 A1 | 8/1994 |
| EP | 0662515 A1 | 7/1995 |
| EP | 0773296 A1 | 5/1997 |
| EP | 1010748 A1 | 6/2000 |
| EP | 1223219 A2 | 7/2002 |
| FR | 2833490 A1 | 6/2003 |
| GB | 195876 A | 4/1923 |
| GB | 2235457 A | 3/1991 |
| JP | 60206893 | 10/1985 |
| JP | 06327481 | 11/1994 |
| JP | 07289261 | 11/1995 |
| JP | 08266281 | 10/1996 |
| WO | WO-9409094 A1 | 4/1994 |
| WO | WO-9641882 A1 | 12/1996 |
| WO | WO-0023039 A2 | 4/2000 |
| WO | WO-00/58342 A1 | 10/2000 |
| WO | WO-0138476 A1 | 5/2001 |
| WO | WO-01/57528 A | 8/2001 |
| WO | WO-0157066 A2 | 8/2001 |
| WO | WO-0160916 A1 | 8/2001 |
| WO | WO-0220651 A2 | 3/2002 |
| WO | WO-0246342 A2 | 6/2002 |
| WO | WO-0246369 A2 | 6/2002 |
| WO | WO-03018673 A | 3/2003 |
| WO | WO-03031500 A1 | 4/2003 |
| WO | WO-03053383 A2 | 7/2003 |
| WO | WO-03080137 A1 | 10/2003 |
| WO | WO-2004000880 A1 | 12/2003 |
| WO | WO-2005033316 A2 | 4/2005 |
| WO | WO-2005068087 A2 | 7/2005 |
| WO | WO-2005115306 A2 | 12/2005 |
| WO | WO-2006/082251 A2 | 8/2006 |
| WO | WO-2006082253 A2 | 8/2006 |
| WO | WO-2006/103225 A1 | 10/2006 |
| WO | WO-2006/103230 A1 | 10/2006 |
| WO | WO-2006/103251 A1 | 10/2006 |
| WO | WO-2006103215 A1 | 10/2006 |
| WO | WO-2006103252 A2 | 10/2006 |
| WO | WO-2006103253 A2 | 10/2006 |
| WO | WO-2006131555 A1 | 12/2006 |

(Continued)

OTHER PUBLICATIONS

Nakari-Setala et al., Applied and Environmental Microbiology, Jul. 2002, pp. 3385-3391.*

(Continued)

*Primary Examiner* — Suzanne M. Noakes
(74) *Attorney, Agent, or Firm* — Connolly Bove Lodge & Hutz LLP

(57) ABSTRACT

Polypeptides of the general structural formula (I)

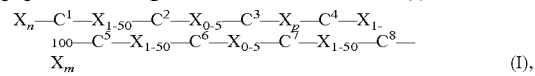

production and use thereof.

10 Claims, 7 Drawing Sheets

FOREIGN PATENT DOCUMENTS

| WO | WO-2006131564 A2 | 12/2006 |
|----|------------------|---------|
| WO | WO-2006136607 A2 | 12/2006 |
| WO | WO-2007006765 A1 | 1/2007 |
| WO | WO-2007014897 A1 | 2/2007 |
| WO | WO-2007042487 A2 | 4/2007 |

OTHER PUBLICATIONS

Stringer, M. A., et al, "dewA Encodes a Fungal Hydrophobin Component of the *Aspergillus* Spore Wall", Molecular Microbiology, 1995, vol. 16, No. 1, pp. 33-44.

Belitsky, B. R., "Physical and Enzymological Interaction of *Bacillus subtilis* Proteins Required for De Novo Pyridoxal 5' Phosphate Biosynthesis", Journal of Bacteriology, 2004, vol. 186, No. 4, pp. 1191-1196.

Wösten, H. A. B., "Hydrophobins: Multipurpose Proteins", Annu. Rev. Microbiol., 2001, vol. 55, pp. 625-646.

Janssen, M.I., at al., Coating with Genetic Engineered Hydrophobin Promotes Growth of Fibroblasts on a Hydrophobic Solid, Biomaterials, 2002, vol. 23, pp. 4847-4854.

Ananichev, A.V., et al., "Immobilization of Glucose Isomerase by Adsorption on Porous Silochrome Under Vacuum", Prikladnaya Biokhimiya I Mikrobiologiya, 1984, vol. 20, No. 4, pp. 458-463.

Scholtmeijer, K. et al., "Fungal hydrophobins in medical and technical applications", Applied Microbiology & Biotechnology, 2001, vol. 56, pp. 1-8.

Hektor, H. J., et al., "Hydrophobins: proteins with potential", Current Opinion in Biotechnology, 2005, vol. 16, pp. 434-439.

De Vocht, M. L., et al., "Structural and functional role of the disulfide bridges in the hydrophobin SC3", Journal of Biological Chemistry, 2000, vol. 275, No. 37, pp. 28428-28432.

Hider, G.C., "A relatively simple test for the direct determination of the cysteine content in photographic gelatin using a thiol-specific fluorogenic reagent", The Imaging Science Journal, 1997, vol. 45, pp. 162-166.

Bauer, J. A., et al., "Three-dimensional structure of YaaE from *Bacillus subtilis*, a glutaminase implicated in pyridoxal-5'-phosphate biosynthesis", Journal Of Biological Chemistry, 2004, vol. 279, No. 4, pp. 2704-2711.

Imai, Y., et al., "The Fission Yeast Mating Pheromone P-factor: its Molecular Structure, Gene Structure, and Ability to Induce Gene Expression and $G_1$ Arrest in the Mating Partner", Development, 1994, vol. 8, pp. 328-338.

Nakari-Setala, T., et al., "Expression of a Fungal Hydrophobin in the *Saccharomyces cerevisiae* Cell Wall: Effect on Cell Surface Properties and Immobilization", Applied and Environmental Microbiology, 2002, vol. 68, No. 7, pp. 3385-3391.

Linder, M., at al., "Surface Adhesion of Fusion Proteins Containing the Hydrophobins HFBI and HFBII from *Trichoderma reesei*", Protein Science, 2002, vol. 11, pp. 2257-2266.

Corvis, Y., et al., "Preparing catalytic surfaces for sensing applications by immobilizing enzymes via hydrophobin layers", Anal. Chem., 2005, vol. 77, pp. 1622-1630.

Scholtmeijer, K., et al., "Surface modifications created by using engineered hydrophobins", Applied and Environmental Microbiology, 2002, vol. 68, No. 3, pp. 1367-1373.

Claessen, D., et al., "A novel class of secreted hydrophobic proteins is involved in aerial hyphae formation in *Streptomyces coelicolor* by forming amyloid-like fibrils", Genes & Development, 2003, vol. 17, pp. 1714-1726.

Elliot, M. A., et al., "The chaplins: a family of hydrophobic cell-surface proteins involved in aerial mycelium formation in *Streptomyces coelicolor*", Genes & Development, 2003, vol. 17, pp. 1727-1740.

Van Wetter, M-A., et al., "SC3 and SC4 hydrophobins have distinct roles in formation of aerial structures in dikaryons of *Schizophyllum commune*", Molecular Microbiology, 2000, vol. 36, No. 1, pp. 201-210.

Kershaw, M. J., et al., "Hydrophobins and repellents: proteins with fundamental roles in fungal morphogenesis", fungal Genetics and Biology, 1998, vol. 23, pp. 18-33.

Wösten, H. A. B., et al., "How a fungus escapes the water to grow into the air", Curr. Biol., 1999, vol. 19, pp. 85-88.

Bell-Pedersen, D., et al., "The *Neurospora* circadian clock-controlled gene, *ccg-2*, is allelic to *eas* and encodes a fungal hydrophobin required for formation of the conidial rodlet layer", Genes & Development, 1992, vol. 6, pp. 2382-2394.

Lugones, L . G., et al., "Hydrophobins line air channels in fruiting bodies of *Schizophyllum commune* and *Agaricus bisporus*.", Mycol. Res., 1999. vol. 103, No. 5, pp. 635-340.

Hamer, J. E., et al., "Infection-related development in the rice blast fungus *Magnaporthe grisea*", Curr. Opinion Microiol., 1998, vol. 1, pp. 693-697.

\* cited by examiner

Figure 2
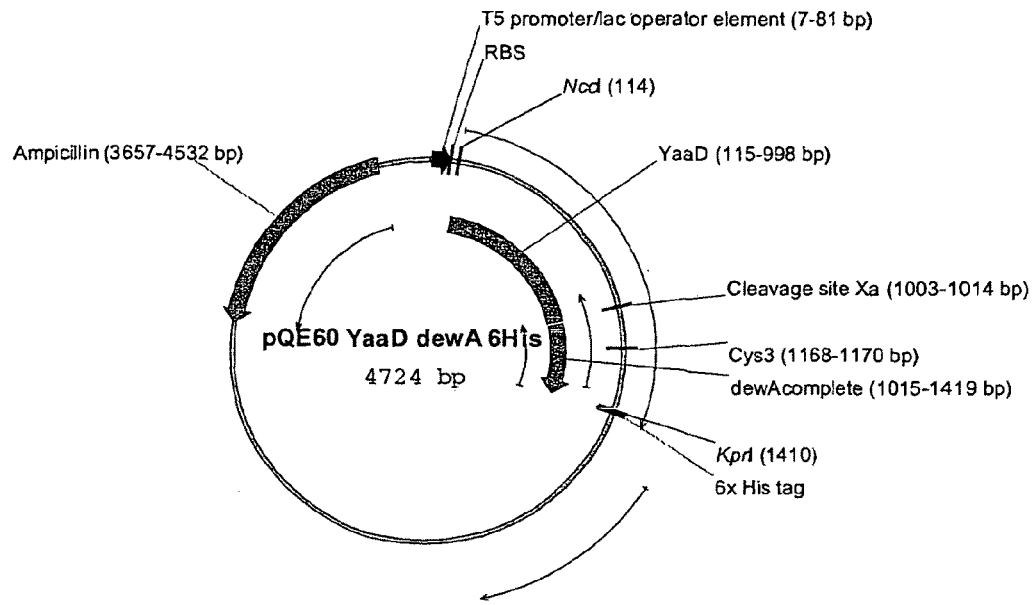
pQE60 YaaD-dewA Cys3-T7 novispirin
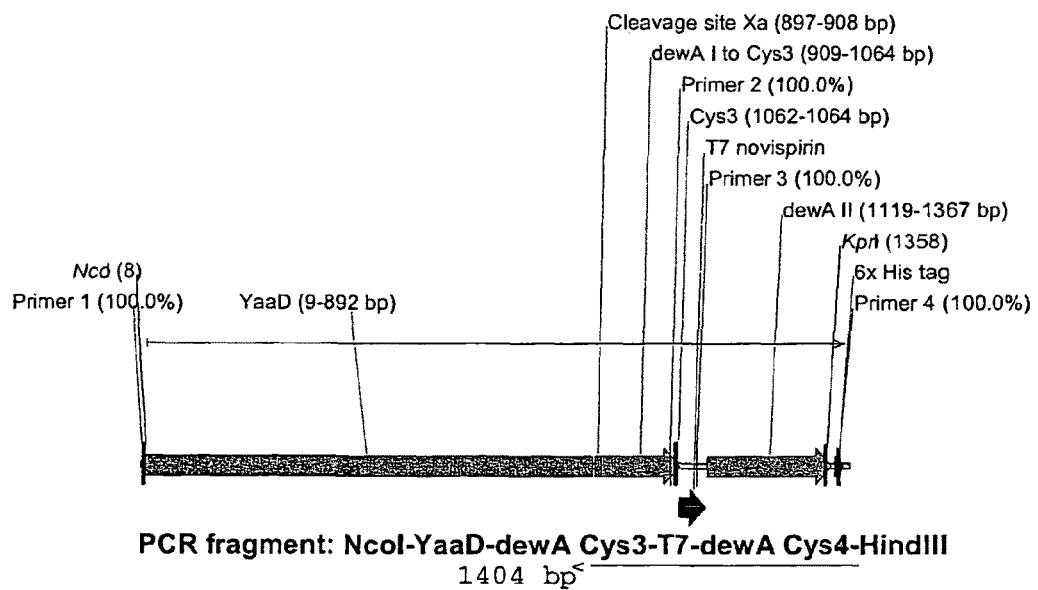

Figure 3

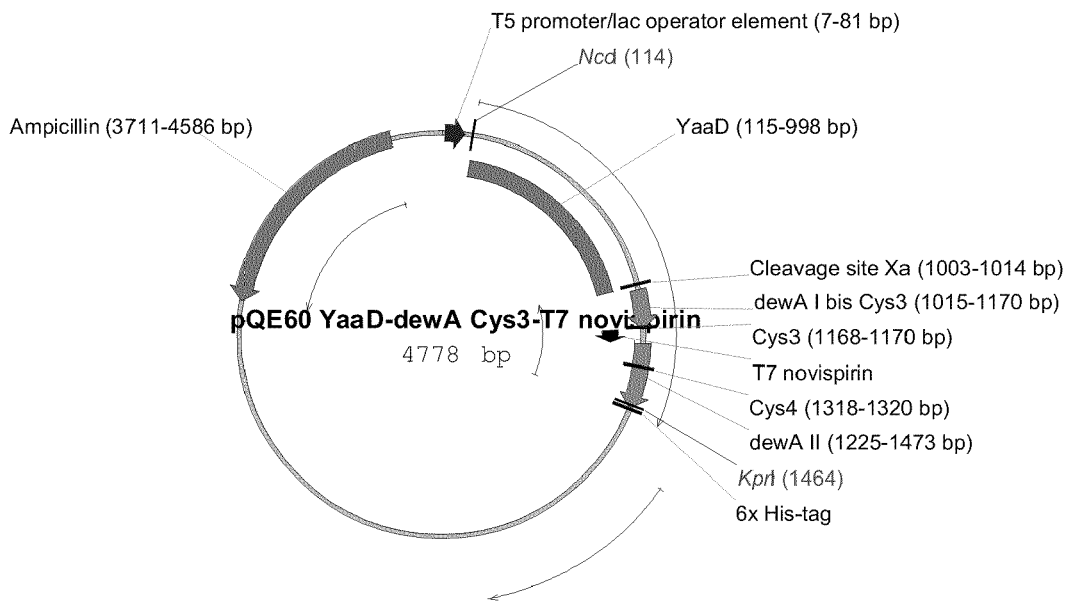

YaaD-dewA Cys3-T7-dewA 6His
461 aa

```
           YaaD
     ~~~~~~~~~~~~~~~~~~~~~~~~~~~~~~~~~~~~~~~~~~~~~~~~~~~~~~
  1  MAQTGTERVK RGMAEMQKGG VIMDVINAEQ AKIAEEAGAV AVMALERVPA
           YaaD
     ~~~~~~~~~~~~~~~~~~~~~~~~~~~~~~~~~~~~~~~~~~~~~~~~~~~~~~
 51  DIRAAGGVAR MADPTIVEEV MNAVSIPVMA KARIGHIVEA RVLEAMGVDY
           YaaD
     ~~~~~~~~~~~~~~~~~~~~~~~~~~~~~~~~~~~~~~~~~~~~~~~~~~~~~~
101  IDESEVLTPA DEEFHLNKNE YTVPFVCGCR DLGEATRRIA EGASMLRTKG
           YaaD
     ~~~~~~~~~~~~~~~~~~~~~~~~~~~~~~~~~~~~~~~~~~~~~~~~~~~~~~
151  EPGTGNIVEA VRHMRKVNAQ VRKVVAMSED ELMTEAKNLG APYELLLQIK
           YaaD
     ~~~~~~~~~~~~~~~~~~~~~~~~~~~~~~~~~~~~~~~~~~~~~~~~~~~~~~
201  KDGKLPVVNF AAGGVATPAD AALMMQLGAD GVFVGSGIFK SDNPAKFAKA
           YaaD
     ~~~~~~~~~~~~~~~~~~~~~~~~~~~~~~~~~~~~~~~~~~~~~~~~~~~~~~
251  IVEATTHFTD YKLIAELSKE LGTAMKGIEI SNLLPEQRMQ ERGWRSIEGR
          dewA I
     ~~~~~~~~~~~~~~~~~~~~~~~~~~~~~~~~~~~~~~~~~~~~~~~~~~~~~~
301  MRFIVSLLAF TAAATATALP ASAAKNAKLA TSAAFAKQAE GTTCNVGSIA
```

Figure 3 (cont.)

```
                     T7
         ~~~~~~~~~~~~~~~~~~~~
         dewA I                          dewA II
         ~~                      ~~~~~~~~~~~~~~~~~~~~~~~~~~~~~~~
    351  CCKNLRRITR KIIHIIKKYG NSPAETNNDS LLSGLLGAGL LNGLSGNTGS
                                   dewA II
         ~~~~~~~~~~~~~~~~~~~~~~~~~~~~~~~~~~~~~~~~~~~~~~~~~~~~~~~
    401  ACAKASLIDQ LGLLALVDHT EEGPVCKNIV ACCPEGTTNC VAVDNAGAGT
                 6His
              ~~~~~~~
         dewA II
         ~~~
    451    KAEGSHHHHH H (SEQ ID NO:42)
```

Figure 5

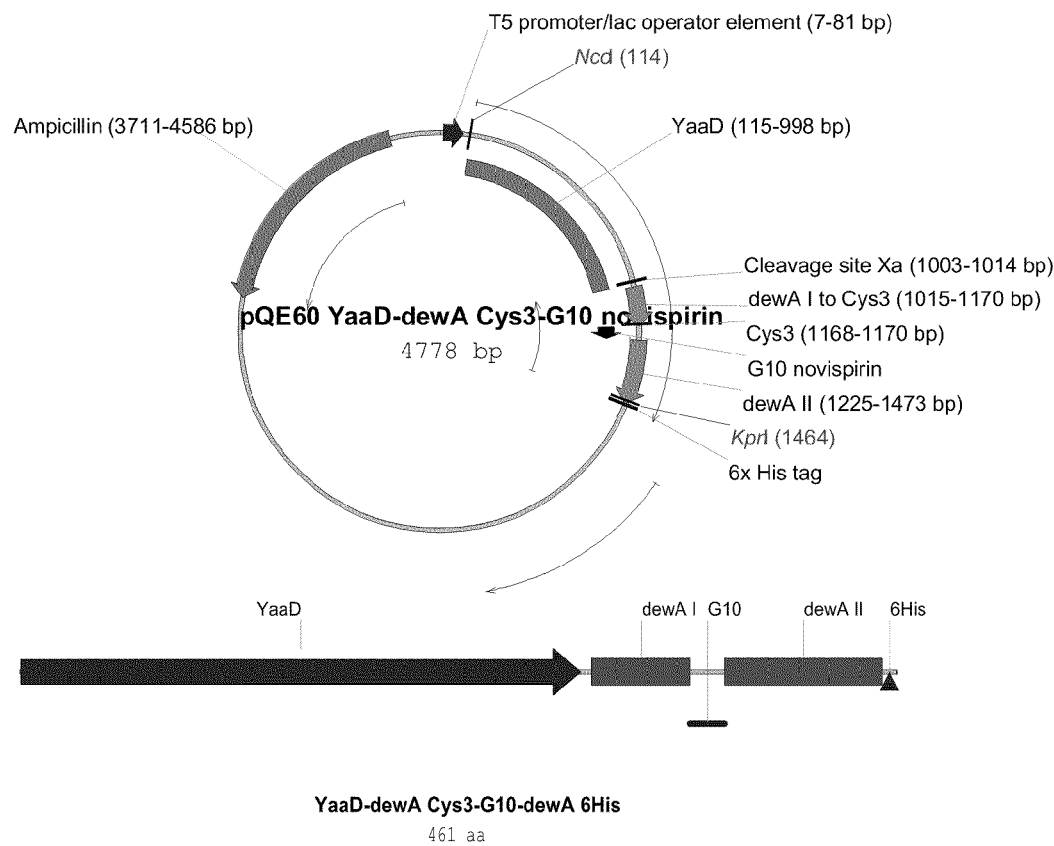

YaaD-dewA Cys3-G10-dewA 6His
461 aa

YaaD

```
  1  MAQTCTERVK RCMAEMQKCC VIMDVINAEQ AKIAEEACAV AVMALERVPA
                                YaaD

51  DTRAAGGVAR MADPTTVEEV MNAVSTPVMA KARIGHTVEA RVLEAMGVDY
                                YaaD

101  IDESEVLTPA DEEFHLNKNE YTVPFVCGCR DLGEATRRIA EGASMLRIKG
                                YaaD

151  EPGTGNIVEA VRHMRKVNAQ VRKVVAMSED ELMTEAKNLG APYELLLQIK
                                YaaD

201  KDGKLPVVNF AAGGVATPAD AALMMQLGAD GVFVGSGIFK SDNPAKFAKA
                                YaaD

251  IVEATTHFTD YKLIAELSKE LGTAMKGIEI SNLLPEQRMQ ERGWRSIEGR
                                dewA I 301  MRFIVSLLAF TAAATATALP ASAAKNAKLA TSAAFAKQAE GTTCNVGSIA
                      G10
         dewA I                        dewA II 351  CCKNLRRIIR KGIHIIKKYG NSPAETNNDS LLSGLLGAGL LNGLSGNTGS
                               dewA II
```

Figure 5 (cont.)

```
         ~~~~~~~~~~~~~~~~~~~~~~~~~~~~~~~~~~~~~~~~~~~~~~~~~~~~
    401  ACAKASLIDQ LGLLALVDHT EEGPVCKNIV ACCPEGTTNC VAVDNAGAGT
              6His
            ~~~~~~
         dewA II
         ~~~
    451   KAEGSHHHHH H (SEQ ID NO:43)
```

CYSTEINE-DEPLETED HYDROPHOBIN FUSION PROTEINS, THEIR PRODUCTION AND USE THEREOF

RELATED APPLICATIONS

This application is a national stage application under 35 U.S.C. 371 of PCT/EP2006/063066, filed Jun. 9, 2006, and which claims benefit of German application 10 2005 027 139.1, filed Jun. 10, 2005.

The present invention relates to novel hydrophobin fusion proteins, their production and use thereof.

PRIOR ART

Hydrophobins are small proteins of about 100 AA which are characteristic for filamentous fungi and do not occur in other organisms. Recently, hydrophobin-like proteins were found in *Streptomyces coelicolor* that are referred to as "Chaplins" and likewise have highly surface-active properties. Chaplins may assemble at water-air interfaces to give amyloid-like fibrils (Classen et al. 2003 Genes Dev 1714-1726; Elliot et al. 2003, Genes Dev. 17, 1727-1740).

Hydrophobins are distributed in a water-insoluble form on the surface of various fungal structures such as, for example, aerial hyphae, spores, fruit bodies. The genes for hydrophobins were isolated from ascomycetes, deuteromycetes and basidiomycetes. Some fungi comprise more than one hydrophobin gene, for example *Schizophyllum commune, Coprinus cinereus, Aspergillus nidulans*. Evidently, various hydrophobins are involved in different stages of fungal development. Said hydrophobins are presumably responsible for different functions (van Wetter et al., 2000, Mol. Microbiol., 36, 201-210; Kershaw et al. 1998, Fungal Genet. Biol, 1998, 23, 18-33).

A biological function of hydrophobins which is described in addition to reducing the surface tension of water for generating aerial hyphae is also the hydrophobization of spores (Wösten et al. 1999, Curr. Biol., 19, 1985-88; Bell et al. 1992, Genes Dev., 6, 2382-2394). Furthermore, hydrophobins are used for lining gas channels in fruit bodies of lichens and as components in the system of identifying plant surfaces by fungal pathogens (Lugones et al. 1999, Mycol. Res., 103, 635-640; Hamer & Talbot 1998, Curr. Opinion Microbiol., Volume 1, 693-697).

Complementation experiments have demonstrated that hydrophobins can be functionally replaced up to a certain degree within a single class.

Previously disclosed hydrophobins can be prepared only with moderate yield and purity using customary protein-chemical purification and isolation methods. Attempts of providing larger amounts of hydrophobins with the aid of genetic methods have also not been successful up to now.

OBJECT OF THE INVENTION

It was the object to provide novel hydrophobins and methods of production thereof, which allow hydrophobins to be produced economically and used in various technical fields.

BRIEF DESCRIPTION OF THE DRAWINGS

FIG. 2 depicts pQE60 YaaD-dewA Cys3-T7 novispirin.

FIG. 3 depicts pQE60 YaaD-dewA Cys3-T7 novispirin and YaaD-dewA Cys3-T7-dewA 6His FIG. 5 depicts pQE60 YaaD-dewA Cys3-G10 novispirin and YaaD-dewA Cys3-G10-dewA 6His

DESCRIPTION OF THE INVENTION

Figure 1:
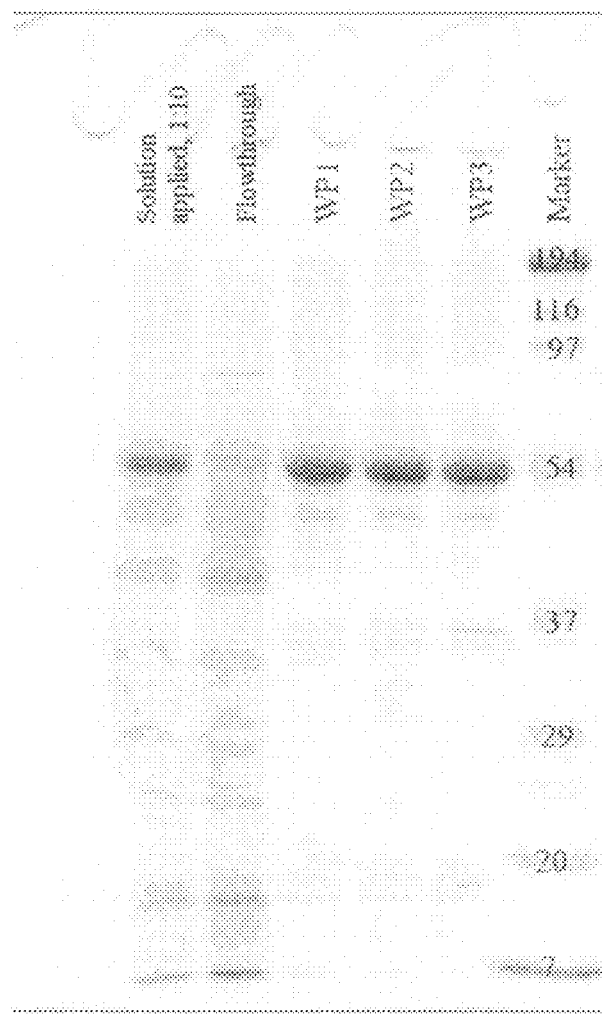
FIG. 1 depicts an purification of the hydrophobin of the invention.

The invention relates to polypeptides of the general structural formula (I)

$$X_n-C^1-X_{1\text{-}50}-C^2-X_{0\text{-}5}-C^3-X_p-C^4-X_{1\text{-}100}-C^5-X_{1\text{-}50}-C^6-X_{0\text{-}5}-C^7-X_{1\text{-}50}-C^8-X_m \quad (I),$$

where X may be any of the 20 naturally occurring amino acids (Phe, Leu, Ser, Tyr, Cys, Trp, Pro, His, Gln, Arg, Ile, Met, Thr, Asn, Lys, Val, Ala, Asp, Glu, Gly) and the indices at X indicate the number of amino acids, with the indices n and m being numbers between 0 and 500, preferably between 15 and 300, p being a number between 1 and 250, preferably between 1-100 and C being cysteine, alanine, serine, glycine, methionine or threonine, with at least four of the residues designated by C being cysteine, with the proviso that at least one of the peptide sequences abbreviated as $X_n$ or $X_m$ or $X_p$ is a peptide sequence of at least 20 amino acids in length which is not linked to a hydrophobin naturally, which polypeptides change the contact angle by at least 200 after coating of a glass surface.

The amino acids designated by $C^1$ to $C^8$ are preferably cysteines, but they may also be replaced with other similarly bulky amino acids, preferably alanine, serine, threonine, methionine or glycine. However, at least four, preferably at least 5, particularly preferably at least 6, and in particular at least 7, of the $C^1$ to $C^8$ positions should comprise cysteines. Cysteines may either be in the reduced form or form disulfide bridges with one another in the proteins of the invention. Particular preference is given to the intramolecular formation of C—C bridges, in particular those having at least one, preferably 2, particularly preferably 3, and very particularly preferably 4, intramolecular disulfide bridges. Advantageously, when replacing cysteines with similarly bulky amino acids, as described above, pairs of those C positions which can form intramolecular disulfide bridges between them are replaced.

If cysteines, serines, alanines, glycines, methionines or threonines are also used in the positions designated by X, the numbering of the individual cysteine positions in the general formulae may change accordingly.

Particularly advantageous polypeptides are those of the general formula (II)

$$X_n-C^1-X_{3\text{-}25}-C^2-X_{0\text{-}2}-C^3-X_{5\text{-}50}-C^4-X_{2\text{-}35}-C^5-X_{2\text{-}15}-C^6-X_{0\text{-}2}-C^7-X_{3\text{-}35}-C^8-X_m \quad (II)$$

where X may be any of the 20 naturally occurring amino acids (Phe, Leu, Ser, Tyr, Cys, Trp, Pro, His, Gln, Arg, Ile, Met, Thr, Asn, Lys, Val, Ala, Asp, Glu, Gly) and the indices at X indicate the number of amino acids, with the indices n and m being numbers between 2 and 300 and C being cysteine, alanine, serine, glycine, methionine or threonine, with at least four of the residues designated by C being cysteine, with the proviso that at least one of the peptide sequences abbreviated as $X_n$ or $X_m$ is a peptide sequence of at least 35 amino acids in length which is not linked to a hydrophobin naturally, which polypeptides change the contact angle by at least 200 after coating of a glass surface.

Very particularly advantageous are those polypeptides of the general formula (III)

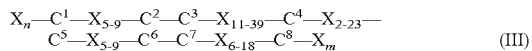
$$X_n\text{—}C^1\text{—}X_{5-9}\text{—}C^2\text{—}C^3\text{—}X_{11-39}\text{—}C^4\text{—}X_{2-23}\text{—}$$
$$C^5\text{—}X_{5-9}\text{—}C^6\text{—}C^7\text{—}X_{6-18}\text{—}C^8\text{—}X_m \quad (III)$$

where X may be any of the 20 naturally occurring amino acids (Phe, Leu, Ser, Tyr, Cys, Trp, Pro, His, Gln, Arg, Ile, Met, Thr, Asn, Lys, Val, Ala, Asp, Glu, Gly) and the indices at X indicate the number of amino acids, with the indices n and m being numbers between 0 and 200 and C being cysteine, alanine, serine, glycine, methionine or threonine, with at least six of the residues designated by C being cysteine, with the proviso that at least one of the peptide sequences abbreviated as $X_n$ or $X_m$ is a peptide sequence of at least 40 amino acids in length which is not linked to a hydrophobin naturally, which polypeptides change the contact angle by at least 20° after coating of a glass surface.

Preferred embodiments of the described invention are polypeptides having the general structural formula (I), (II) or (III), this structural formula comprising at least one Class I hydrophobin, preferably at least one dewA, rodA, hypA, hypB, sc3, basf1, basf2, hydrophobin, or parts or derivatives thereof. Said hydrophobins are structurally characterized in the sequence listing below. It is also possible for a plurality, preferably 2 or 3, structurally identical or different hydrophobins to be linked to one another and to a corresponding suitable polypeptide sequence which is not connected with a hydrophobin naturally.

Particularly preferred embodiments of the present invention are the novel proteins having the polypeptide sequences depicted in SEQ ID NO: 20, 22, 24 and the nucleic acid sequences coding therefor, in particular the sequences as defined in SEQ ID NO: 19, 21, 23. Particularly preferred embodiments are also proteins which arise from substitution, insertion or deletion of at least one, up to 10, preferably 5, particularly preferably 5% of all, amino acids, starting from the polypeptide sequences depicted in SEQ ID NO: 22, 22, or 24, and which still have at least 50% of the biological property of the starting proteins. Biological property of the proteins here means the change in the contact angle, as described in Example 10.

The proteins of the invention have in at least one position abbreviated by $X_n$ or $X_m$ or $X_p$ a polypeptide sequence comprising at least 20, preferably at least 35, particularly preferably at least 50, and in particular at least 100, amino acids (also referred to as fusion partner hereinbelow), which is not linked naturally to a hydrophobin. This is intended to express the fact that the proteins of the invention consist of a hydrophobin moiety and a fusion partner moiety which do not occur together in this form in nature.

The fusion partner moiety may be selected from a multiplicity of proteins. It is also possible to link a plurality of fusion partners to one hydrophobin moiety, for example at the amino terminus ($X_n$) and at the carboxy terminus ($X_m$) or in the middle ($X_p$) of the hydrophobin moiety. However, it is also possible to link, for example, two fusion partners to a single position ($X_n$ or $X_m$) of the protein of the invention.

Particularly preferred fusion partners are those polypeptide sequences which enable the protein of the invention to coat glass surfaces and cause the protein-treated glass surface to become resistant to a treatment with detergents, as described in detail in the experimental section (Example 10) (e.g. 1% SDS/80° C./10 min).

Particularly suitable fusion partners are polypeptides which occur naturally in microorganisms, in particular in *E. coli* or *Bacillus subtilis*. Examples of such fusion partners are the sequences yaad (SEQ ID NO: 15 and 16), yaae (SEQ ID NO: 17 and 18) and thioredoxin. Very useful are also fragments or derivatives of said sequences which comprise only part, preferably 10-90%, particularly preferably 25-75%, of said sequences. Preference is given here to a deletion at the C-terminal end, for example a yaad fragment which consists of only the first 75 N-terminal amino acids, or in which individual amino acids or nucleotides have been altered in comparison with said sequence. For example, additional amino acids, in particular two additional amino acids, preferably the amino acids Arg, Ser, may be attached to the C-terminal end of the yaad and yaae sequences. It is also possible with preference for additional amino acids, for example amino acid No. 2 (Gly) in SEQ ID NO: 17 and 18, to be inserted in the yaae sequence compared to the naturally occurring sequence.

Other examples of fusion partners, in particular those at position $X_p$ in the general formula (I), are enzymatically active domains, antimicrobial domains, polypeptide sequences acting as agonists/antagonists on receptors, colorants, flavorings and aromas, metal-binding domains. It is furthermore possible to produce specifically coupling sites for covalent binding of various active compounds and effectors. For example, additional lysines may be inserted into this loop in order to couple active compounds and effectors specifically to the hydrophobin molecular backbone via the primary amino group with the aid of the heterobifunctional linkers known to the skilled worker.

Furthermore, it is also possible to insert at the junctions of two fusion partners additional amino acids which are the result of either newly creating or inactivating recognition sites for restriction endonucleases at the nucleic acid level.

It is further still possible for the polypeptide sequence of the proteins of the invention to be modified, for example by glycosylation, acetylation or else by chemical crosslinking, for example with glutardialdehyde.

One property of the proteins of the invention is the change in surface properties, when said surfaces are coated with said proteins. Said change in the surface properties can be determined experimentally by measuring the contact angle of a water drop, before and after coating of the surface with the protein of the invention, and determining the difference of the two measurements.

The exact experimental conditions for measuring the contact angle are laid down in the experimental section in Example 10. Under these conditions, the proteins of the invention have the property of increasing the contact angle by at least 20, preferably 25, particularly preferably 30 degrees.

The positions of polar and unpolar amino acids in the hydrophobin moiety of the previously disclosed hydrophobins are conserved, resulting in a characteristic hydrophobicity plot. Differences in the biophysical properties and in hydrophobicity caused the previously disclosed hydrophobins to be divided into two classes, I and II (Wessels et al. 1994, Ann. Rev. Phytopathol., 32, 413-437).

The assembled membranes of Class I hydrophobins are insoluble to a high degree (even with respect to 1% SDS at elevated temperature) and can be dissociated again only by concentrated trifluoroacetic acid (TFA) or formic acid. In contrast, the assembled forms of Class II hydrophobins are less stable. They may be dissolved again even by 60% strength ethanol or 1% SDS (at room temperature). This high stability to solvents and detergents is a particular property of hydrophobins and distiguishes coatings with the polypeptides of the invention from "unspecific" protein coatings as formed by a multiplicity of proteins on surfaces.

A comparison of the amino acid sequences reveals that the length of the region between cysteine C³ and C⁴ is distinctly shorter in Class II hydrophobins than in Class I hydrophobins.

Furthermore, Class II hydrophobins have more charged amino acids than Class I.

The invention further relates to methods for producing the proteins of the invention. These polypeptides can be produced chemically by known methods of peptide synthesis, for example solid phase synthesis according to Merrifield.

Particularly useful, however, are genetic methods in which two nucleic acid sequences, in particular DNA sequences, coding for the fusion partner and the hydrophobin moiety, respectively, are combined in such a way that gene expression of the combined nucleic acid sequence generates the desired protein in a host organism.

Suitable host organisms (producer organisms) here may be prokaryotes (including Archaea) or eukaryotes, particularly bacteria including halobacteria and methanococci, fungi, insect cells, plant cells and mammalian cells, particularly preferably *Escherichia coli, Bacillus subtilis, Bacillus megaterium, Aspergillus oryzea, Aspergillus nidulans, Aspergillus niger, Pichia pastoris, Pseudomonas* spec., Lactobacillen, *Hansenula polymorpha, Trichoderma reesei*, SF9 (or related cells), and others.

The invention moreover relates to expression constructs comprising a nucleic acid sequence coding for a polypeptide of the invention under the genetic control of regulatory nucleic acid sequences, and also vectors comprising at least one of said expression constructs.

Preference is given to such constructs of the invention comprising a promoter 5' upstream of the particular coding sequence and a terminator sequence 3' downstream, and also, if appropriate, further customary regulatory elements, in each case operatively linked to said coding sequence.

An "operative linkage" means the sequential arrangement of promoter, coding sequence, terminator and, if appropriate, further regulatory elements in such a way that each of the regulatory elements is able to fulfill its function in accordance with its intended use in connection with expressing the coding sequence.

Examples of sequences which can be operatively linked are targeting sequences and also enhancers, polyadenylation signals and the like. Further regulatory elements comprise selectable markers, amplification signals, origins of replication and the like. Examples of suitable regulatory sequences are described in Goeddel, Gene Expression Technology: Methods in Enzymology 185, Academic Press, San Diego, Calif. (1990).

In addition to these regulatory sequences, the natural regulation of these sequences may still be present upstream of the actual structural genes and, if appropriate, have been genetically modified such that the natural regulation has been switched off and expression of the genes has been increased.

A preferred nucleic acid construct advantageously also comprises one or more of the enhancer sequences already mentioned which are functionally linked to the promoter and enable expression of the nucleic acid sequence to be increased. Additional advantageous sequences such as further regulatory elements or terminators may also be inserted at the 3' end of the DNA sequences.

The nucleic acids of the invention may be present in the construct in one or more copies. The construct may comprise still further markers such as antibiotic resistances or genes which complement auxotrophies, for selecting for the construct, if appropriate.

Examples of regulatory sequences which are advantageous for the method of the invention are present in promoters such as the cos, tac, trp, tet, trp-tet, lpp, lac, lpp-lac, lacIq-T7, T5, T3, gal, trc, ara, rhaP(rhaPBAD) SP6, lambda-PR or lambda-P promoter, which are advantageously used in Gram-negative bacteria. Further examples of advantageous regulatory sequences are present in the Gram-positive promoters amy and SP02, in the yeast or fungal promoters ADC1, MFalpha, AC, P-60, CYC1, GAPDH, TEF, rp28, ADH.

It is also possible to use artificial promoters for regulation.

To be expressed in a host organism, the nucleic acid construct is advantageously inserted into a vector such as, for example, a plasmid or a phage, which enables the genes to be expressed optimally in the host. Apart from plasmids and phages, vectors also mean any other vectors known to the skilled worker, i.e., for example, viruses such as SV40, CMV, baculovirus and adenovirus, transposons, IS elements, phasmids, cosmids, and linear or circular DNA and also the *Agrobacterium* system.

These vectors may either replicate autonomously in the host organism or be replicated chromosomally. These vectors constitute another embodiment of the invention. Examples of suitable plasmids are pLG338, pACYC184, pBR322, pUC18, pUC19, pKC30, pRep4, pHS1, pKK223-3, pDHE19.2, pHS2, pPLc236, pMBL24, pLG200, pUR290, pIN-III'3-B1, tgt11 or pBdCI in *E. coli*, pIJ101, pIJ364, pIJ702 or pIJ361 in *Streptomyces*, pUB110, pC194 or pBD214 in *Bacillus*, pSA77 or pAJ667 in *Corynebacterium*, pALS1, pIL2 or pBB116 in fungi, 2alpha, pAG-1, YEp6, YEp13 or pEMBLYe23 in yeasts or pLGV23, pGHlac+, pBIN19, pAK2004 or pDH51 in plants. Said plasmids are a small selection of the possible plasmids. Further plasmids are well known to the skilled worker and can be found, for example, in the book Cloning Vectors (Eds. Pouwels P. H. et al. Elsevier, Amsterdam-New York-Oxford, 1985, ISBN 0 444 904018).

Advantageously, the nucleic acid construct additionally comprises, for the purpose of expressing the other genes present, also 3'- and/or 5'-terminal regulatory sequences for increasing expression which are selected for optimal expression depending on the host organism and gene or genes selected.

These regulatory sequences are intended to enable the genes and protein expression to be expressed specifically. Depending on the host organism, this may mean, for example, that the gene is expressed or overexpressed only after induction or that it is expressed and/or overexpressed immediately.

In this connection, the regulatory sequences or factors may preferably have a beneficial influence on, and thereby increase, gene expression of the introduced genes. Thus the regulatory elements can advantageously be enhanced at the transcriptional level by using strong transcription signals such as promoters and/or enhancers. Apart from that, however, it is also possible to enhance translation by improving mRNA stability, for example.

In another embodiment of the vector, the vector comprising the nucleic acid construct of the invention or the nucleic acid of the invention may also advantageously be introduced in the form of a linear DNA into the microorganisms and be integrated into the genome of the host organism by way of heterologous or homologous recombination. Said linear DNA may consist of a linearized vector such as a plasmid, or only of the nucleic acid construct or the nucleic acid of the invention.

In order to achieve optimal expression of heterologous genes in organisms, it is advantageous to modify the nucleic acid sequences according to the specific codon usage employed in the organism. The codon usage can be readily determined on the basis of computer analyses of other known genes of the organism in question.

An expression cassette of the invention is prepared by fusing a suitable promoter to a suitable coding nucleotide sequence and a terminator signal or polyadenylation signal. For this purpose, use is made of familiar recombination and cloning techniques as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and also in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which enables the genes to be expressed optimally in the host. Vectors are well known to the skilled worker and can be found, for example, in "Cloning Vectors" (Pouwels P. H. et al., Eds. Elsevier, Amsterdam-New York-Oxford, 1985).

The vectors of the invention can be used to prepare recombinant microorganisms which are transformed, for example, with at least one vector of the invention and may be used for producing the polypeptides of the invention. Advantageously, the above-described recombinant constructs of the invention are introduced into and expressed in a suitable host system. Preference is given here to using common cloning and transfection methods known to the skilled worker, such as, for example, coprecipitation, protoplast fusion, electroporation, retroviral transfection and the like, in order to express said nucleic acids in the particular expression system. Suitable systems are described, for example, in Current Protocols in Molecular Biology, F. Ausubel et al., Eds. Wiley Interscience, New York 1997, or Sambrook et al. Molecular Cloning: A Laboratory Manual, 2nd Ed., Cold Spring Harbor Laboratory, Cold Spring Harbor Laboratory Press, Cold Spring Harbor, N.Y., 1989.

It is also possible according to the invention to prepare homologously recombined microorganisms. For this purpose, a vector is prepared which comprises at least one section of a gene of the invention or of a coding sequence, into which, if appropriate, at least one amino acid deletion, addition or substitution has been introduced in order to modify, for example functionally disrupt, the sequence of the invention (knockout vector). The introduced sequence may, for example, also be a homolog from a related microorganism or be derived from a mammalian, yeast or insect source. The vector used for homologous recombination may alternatively be designed such that the endogenous gene mutates or is modified in some other way during homologous recombination but still encodes the functional protein (for example, the upstream regulatory region may have been modified in a way which modifies expression of the endogenous protein). The modified section of the gene of the invention is in the homologous recombination vector. The construction of suitable vectors for homologous recombination is described, for example, in Thomas, K. R. and Capecchi, M. R. (1987) Cell 51: 503.

Any prokaryotic or eukaryotic organisms are in principle suitable for being used as recombinant host organisms for the nucleic acid of the invention or to the nucleic acid construct. Advantageously used host organisms are microorganisms such as bacteria, fungi or yeasts. Gram-positive or Gram-negative bacteria, preferably bacteria of the families Enterobacteriaceae, Pseudomonadaceae, Rhizobiaceae, Streptomycetaceae or Nocardiaceae, particularly preferably bacteria of the genera *Escherichia, Pseudomonas, Streptomyces, Nocardia, Burkholderia, Salmonella, Agrobacterium* or *Rhodococcus*, are advantageously used.

Depending on the host organism, the organisms used in the method of the invention are grown or cultured in a manner known to the skilled worker. Microorganisms are usually grown in a liquid medium comprising a carbon source usually in the form of sugars, a nitrogen source usually in the form of organic nitrogen sources such as yeast extract or salts such as ammonium sulfate, trace elements such as iron, manganese, magnesium salts, and, if appropriate, vitamins, at temperatures of between 0 and 100° C., preferably between 10 and 60° C., while being gassed with oxygen. The pH of the nutrient liquid may or may not be maintained here at a fixed value, i.e. regulated during growth. Growth may take place batchwise, semibatchwise or continuously. Nutrients may be introduced initially at the beginning of the fermentation or be subsequently fed in semicontinuously or continuously. The enzymes may be isolated from the organisms using the method described in the examples or be used for the reaction as a crude extract.

The invention furthermore relates to methods of recombinantly producing polypeptides of the invention or functional, biologically active fragments thereof, which methods comprise culturing a polypeptide-producing microorganism, if appropriate inducing expression of said polypeptides and isolating them from the culture. In this way the polypeptides may also be produced on an industrial scale if desired. The recombinant microorganism may be cultured and fermented by known methods. For example, bacteria can be propagated in TB medium or LB medium and at a temperature of from 20 to 40° C. and a pH of from 6 to 9. Suitable culturing conditions are described in detail in, for example, T. Maniatis, E. F. Fritsch and J. Sambrook, Molecular Cloning: A Laboratory Manual, Cold Spring Harbor Laboratory, Cold Spring Harbor, N.Y. (1989).

If the polypeptides are not secreted into the culture medium, the cells are then disrupted and the product is isolated from the lysate by known methods of isolating proteins. The cells may optionally be disrupted by high-frequency ultrasound, by high pressure, for example in a French pressure cell, by osmolysis, by the action of detergents, lytic enzymes or organic solvents, by using homogenizers or by a combination of several of the methods listed.

The polypeptides may be purified by means of known, chromatographic methods such as molecular sieve chromatography (gel filtration), such as Q-Sepharose chromatography, ion exchange chromatography and hydrophobic chromatography, and also by means of other customary methods such as ultrafiltration, crystallization, salting out, dialysis and native gel electrophoresis. Suitable methods are described, for example, in Cooper, F. G., Biochemische Arbeitsmethoden [original title: The tools of biochemistry], Verlag Water de Gruyter, Berlin, New York or in Scopes, R., Protein Purification, Springer Verlag, New York, Heidelberg, Berlin.

It may be advantageous, for the purpose of isolating the recombinant protein, to use vector systems or oligonucleotides which extend the cDNA by particular nucleotide sequences and thereby encode altered polypeptides or fusion proteins which facilitate purification, for example. Examples of such suitable modifications are "tags" acting as anchors, for example the modification known as hexahistidine anchor, or epitopes which can be recognized by antibodies as antigens (described, for example, in Harlow, E. and Lane, D., 1988, Antibodies: A Laboratory Manual. Cold Spring Harbor (N.Y.) Press). Further suitable tags are, for example, HA, calmodulin-BD, GST, MBD; chitin-BD, streptavidin-BD- Avi tag, Flag tag, T7, etc. These anchors may be used for attaching the proteins to a solid support, such as, for example, a polymer matrix which may have been introduced into a chromatographic column, for example, or to a microtiter plate or any other support. The corresponding purification protocols can be obtained from the commercial affinity tag suppliers.

Many hydrophobin-coated fungal surfaces (spores, fruit bodies, mycelium) exhibit microscopically detectable, characteristic structures referred to as "rodlets". Similar rodlets with a thickness of approx. 10 nm may also be detected on hydrophobin-coated hydrophilic surfaces (e.g. glass, mica, etc.) (Wösten et al., 1993, Plant Cell, 5, 1567-1574).

Owing to the extraordinary properties of hydrophobins for the coating of surfaces (e.g. resistant to detergents such as 1% strength SDS solution, for example), these proteins have great potential for numerous industrial applications. Various patent documents mention examples of such applications to which reference is made hereby with respect to the application of hydrophobins.

| No. | Priority | Applicant |
|---|---|---|
| WO 03/10331 | Jul. 23, 2001 | Applied Nanosystems B.V. |
| WO 04/00880 | Jun. 21, 2002 | Applied Nanosystems B.V. |
| WO 03/84508 | Apr. 04, 2002 | Applied Nanosystems B.V. |
| WO 00/40968 | Jan. 05, 1999 | Unilever N.V. (Hindustan Lever Ltd.) |
| EP-B 1 252 516 | Feb. 04, 2000 | Applied Nanosystems B.V. Stichting voor de Technische Wetenschappen |
| EP-B 1257 571 | Feb. 04, 2000 | Applied Nanosystems B.V. |
| WO 01/57066 | Feb. 04, 2000 | Applied Nanosystems B.V. |
| WO 03/10331 | Jul. 23, 2001 | Applied Nanosystems B.V. |
| WO 03/53383 | Dec. 14, 2001 | L'Oreal |

The industrial utilization of hydrophobins, in particular those of Class I, has been unsuccessful up to now, due to lack of an efficient method of production and purification. The previously described methods which start from natural sources (spores, fungal mycelium etc.) only produce amounts of material on the mg scale (e.g. WO 96/41882).

Approaches via recombinant production in various producer organisms likewise proved to be extremely complicated and not very satisfactory.

The hydrophobin proteins of the invention, both in their fused form, i.e. together with the fusion partner moiety, and in isolated form, have the desirable properties of hydrophobins. It is thus possible to use the proteins of the invention both directly as fusion proteins and, after cleaving off and removing the fusion partner, as "pure" hydrophobins.

If the fusion partner is intended to be removed, it is recommended to incorporate a potential cleavage site (specific recognition site for proteases) into the fusion protein between the hydrophobin moiety and the fusion partner moiety. Particularly suitable cleavage sites are those peptide sequences which do not occur anywhere else in the hydrophobin moiety and the fusion partner moiety, which can be readily determined using bioinformation tools. Particularly useful are, for example, BrCN cleavage on methionine or protease-mediated cleavage by factor Xa, enterokinase, thrombin, TEV (tobacco etch virus protease) cleavage.

EXPERIMENTAL SECTION

Example 1

Preliminary Work for yaad-His$_6$/yaaE-His$_6$ Cloning

A polymerase chain reaction was carried out with the aid of oligonucleotides Hal570 and Hal571 (Hal 572/Hal 573). The template DNA used was genomic DNA from the bacterium *Bacillus subtilis*. The PCR fragment obtained comprised the coding sequence of the *Bacillus subtilis* yaaD/yaaE gene and an NcoI or a BglII restriction cleavage site at the ends. The PCR fragment was purified and cleaved with the restriction endonucleases NcoI and BglII. This DNA fragment was used as an insert and cloned into the Qiagen pQE60 vector which had previously been linearized with the restriction endonucleases NcoI and BglII. The vectors obtained in this way, pQE60YAAD#2/pQE60YaaE#5 may be used for expressing proteins consisting of YAAD::HIS$_6$ and, respectively, YAAE::HIS$_6$.

| | |
|---|---|
| Hal570: | gcgcgcccatggctcaaacaggtactga |
| Hal571: | gcagatctccagccgcgttcttgcatac |
| Hal572: | ggccatgggattaacaataggtgtactagg |
| Hal573: | gcagatcttacaagtgccttttgcttatattcc |

Example 2a

Cloning of yaad-Hydrophobin DewA-His$_6$

A polymerase chain reaction was carried out with the aid of oligonucleotides KaM 416 and KaM 417. The template DNA used was genomic DNA from the mold *Aspergillus nidulans*. The PCR fragment obtained comprised the coding sequence of the hydrophobin gene dewA and an N-terminal factor Xa proteinase cleavage site. The PCR fragment was purified and cleaved with the restriction endonuclease BamHI. This DNA fragment was used as an insert and cloned into the pQE60YAAD#2 vector which had previously been linearized with the restriction endonuclease BglII.

The vector thus obtained, #508, may be used for expressing a fusion protein consisting of YAAD::Xa::dewA::HIS$_6$.

| | |
|---|---|
| KaM416: | GCAGCCCATCAGGGATCCCTCAGCCTTGGTACCAGCGC |
| KaM417: | CCCGTAGCTAGTGGATCCATTGAAGGCCGCATGAAGTTCTCCGTCTC-CGC |

Example 2b

Preparation of a Chimeric Fusion Protein Having Antimicrobial Properties

To introduce a peptide sequence having antimicrobial properties, the following cloning strategy was pursued:

Starting from our Yaad-DewA expression plasmid, "pQE60Yaad dewA His", the antimicrobial peptide sequence was inserted by fusion PCR between cysteines 3 and 4.

FIG. 2

1a) PCR region: YaaD-dewA to Cys3 incl. T7 novispirin overhang
Template: pQE60 YaaD dewA 6His Primer:
Primer 1
(AATTAACCATGGCTCAAACA) 20-mer Primer 2
(GCCATATTTTTTAATAATATGAATAATTTTACGGGTAATACGACGCAGGTTTTTGCAGCAAGCGATCGAGCCGA) 74-mer PCR conditions: 55° C., 1118 bp
1b) PCR region: novispirin overhang to 6His/Stop
Template: pQE60 YaaD dewA 6His

```
Primer:
Primer 3
(ATATTATTAAAAAATATGGCAACTCCCCCGCTGAGACCAA) 40-mer

Primer 4
(CTAATTAAGCTTAGTGATGGT) 21-mer
```

PCR conditions: 54° C., 306 bp
2) Annealing PCR
Combine 50 pmol from PCR 1a and 1b and carry out an annealing PCR by means of Pfu-Polymerase (1 min at 95° C., 5 min at 72° C.—10 cycles)
This was followed by adding the outside primers and carrying out a normal 35 cycle PCR.

```
Primer:
Primer 1
(AATTAACCATGGCTCAAACA) 20-mer

Primer 4
(CTAATTAAGCTTAGTGATGGT) 21-mer
```

PCR conditions: 53° C., 1404 bp
3) Ligation
   Vector:pQE60 YaaD dewA 6His
   Digestion with NcoI/KpnI
   Preparative gel, isolating the 3428 bp band
   Insert: Product from annealing PCR
   Digestion with NcoI/KpnI
   Preparative gel, isolating the 1350 bp band
4) Transformation in XL10/TG10 chemocomp. cells
   FIG. 3
pQE60 YaaD dewA Cys3 G10 novispirin
1a) PCR region: YaaD-dewA to Cys3 incl. G10 novispirin overhang
Template: pQE60 YaaD dewA 6His

```
Primer:
Primer 1
(AATTAACCATGGCTCAAACA) 20-mer

Primer 5
(GCCATATTTTTTAATAATATGAATGCCTTTACGAATAATACGACGCA
GGTTTTTGCAGCAAGCGATCGAGCCGA) 74-mer
```

Figure 4:
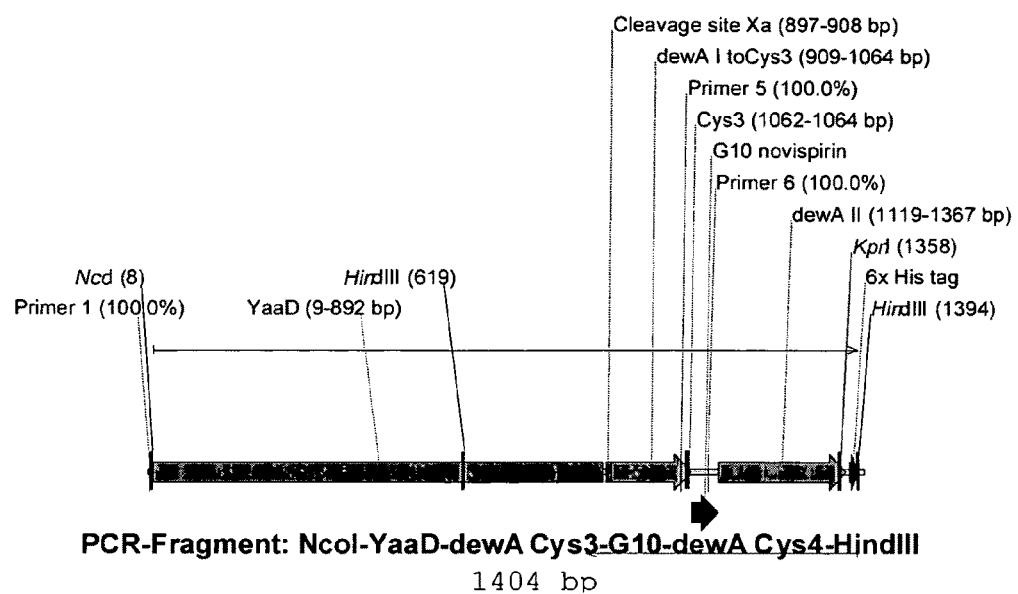
FIG. 4 depicts PCR-Fragment NcoI-YaaD-dewA Cys3-G10-dewA Cys4-HindIII

PCR conditions: 55° C., 1118 bp
1b) PCR region: novispirin overhang to 6His/Stop
   FIG. 4
Template: pQE60 YaaD dewA 6His

```
Primer:
Primer 6
(ATATTATTAAAAAATATGGCAACTCCCCCGCTGAGACCAA) 40-mer

Primer 4
(CTAATTAAGCTTAGTGATGGT) 21-mer
```

PCR conditions: 54° C., 306 bp
2) Annealing PCR
Combine 50 pmol from PCR 1a and 1b and carry out an annealing PCR by means of Pfu-Polymerase (1 min at 95° C., 5 min at 72° C.—10 cycles)

This was followed by adding the outside primers and carrying out a normal 35 cycle PCR.

```
Primer:
Primer 1
(AATTAACCATGGCTCAAACA) 20-mer

Primer 4
(CTAATTAAGCTTAGTGATGGT) 21-mer
```

3) Ligation
   Vector: pQE60 YaaD dewA 6His
   Digestion with NcoI/KpnI
   Preparative gel, isolating the 3428 bp band
   Insert: Product from annealing PCR
   Digestion with NcoI/KpnI
   Preparative gel, isolating the 1350 bp band
4) Transformation in XL10/TG10 Chemocomp. Cells
   FIG. 5
The proteins are purified and evaluated similarly to Examples 8-10.
It was possible to assay the antimicrobial properties:
The assay for antimicrobial action is carried out in 6-well microtiter plates which are charged with the agar required for a corresponding growth (LB, YM). The plates are then inoculated with overnight cultures.
The following microorganisms are used in the assay.
*Bacillus subtilis*
*Bacillus megaterium*
*E. coli* XL1 Blue MR
*Micrococcus luteus*
*Pantoea*
*Kurthia gibs.*
*Pseudomonas* sp.
*Carnobacterium*
*Candida albicans*
*Fusarium oxysporum*
All MO except *Carnobacterium* and *Pseudomonas* are grown as 20 ml cultures in YPD overnight (30° C., 200 rpm); *Carnobacterium* in TSB and *Pseudomonas* in CASO. Twenty μl of the particular bacterial or fungal suspension are applied to each well of the microtiter plate and plated out slightly. The suspension is allowed to soak into the agar to some extent. Then a hydrophobin solution (likewise 20 μl) is applied to the center of the well; incubation of the agar plates at 30° C. in an incubator. First results can be observed already after the overnight culture: antimicrobial action is revealed by way of no growth around the point of application, with the well being completely grown over in the absence of antimicrobial action.

Example 3

Cloning of yaad-Hydrophobin RodA-His$_6$

Plasmid #513 was cloned similarly to plasmid #508 using the oligonucleotides KaM 434 and KaM 435.

```
KaM434:
GCTAAGCGGATCCATTGAAGGCCGCATGAAGTTCTCCATTGCTGC

KaM435:
CCAATGGGGATCCGAGGATGGAGCCAAGGG
```

Example 4

Cloning of yaad-Hydrophobin BASF1-His$_6$

Plasmid #507 was cloned similarly to plasmid #508 using the oligonucleotides KaM 417 and KaM 418.

The template DNA employed was an artificially synthesized DNA sequence, hydrophobin BASF1 (see annex).

```
KaM417:
CCCGTAGCTAGTGGATCCATTGAAGGCCGCATGAAGTTCTCCGTCTC-
CGC

KaM418:
CTGCCAUCAGGGGATCCCATATGGAGGAGGGAGACAG
```

Example 5

Cloning of yaad-Hydrophobin BASF2-His$_6$

Plasmid #506 was cloned similarly to plasmid #508 using the oligonucleotides KaM 417 and KaM 418.
The template DNA employed was an artificially synthesized DNA sequence, hydrophobin BASF2 (see annex).

```
KaM417:
CCCGTAGCTAGTGGATCCATTGAAGGCCGCATGAAGTTCTCCGTCTC-
CGC

KaM418:
CTGCCATTCAGGGGATCCCATATGGAGGAGGGAGACAG
```

Example 6

Cloning of yaad-Hydrophobin SC3-His$_6$

Plasmid #526 was cloned similarly to plasmid #508 using the oligonucleotides KaM464 and KaM465.
The template DNA employed was Schyzophyllum commune cDNA (see annex).

```
KaM464:    CGTTAAGGATCCGAGGATGTTGATGGGGGTGC

KaM465:    GCTAACAGATCTATGTTCGCCCGTCTCCCCGTCGT
```

Example 7

Fermentation of the Recombinant *E. coli* Strain yaad-Hydrophobin DewA-His$_8$ 3 ml of LB liquid medium are inoculated, in a 15 ml Greiner tube, with an *E. coli* strain expressing yaad-hydrophobin DewA-His$_6$. The culture is incubated at 37° C. on a shaker at 200 rpm for 8 h. In each case 2 l l baffled Erlenmeyer flasks containing 250 ml of LB medium (+100 µg/ml ampicillin) are inoculated with in each case 1 ml of the preculture and incubated at 37° C. on a shaker at 180 rpm for 9 h.
13.5 l of LB medium (+100 µg/ml ampicillin) are inoculated, in a 20 l fermenter, with 0.5 l of preculture (OD$_{600\,nm}$1:10 measured against H$_2$O). 140 ml of 100 mM IPTG are added at an OD$_{60\,nm}$ of ~3.5. After 3 h, the fermenter is cooled down to 10° C. and the fermentation broth is removed by centrifugation. The cell pellet is used for further purification.

Example 8

Purification of the Recombinant Hydrophobin Fusion Protein (Purification of Hydrophobin Fusion Proteins Having a C-Terminal His6 Tag)
100 g of cell pellet (100-500 mg of hydrophobin) are admixed to a total volume of 200 ml with 50 mM sodium phosphate buffer, pH 7.5, and resuspended. The suspension is treated with an Ultraturrax type T25 (Janke and Kunkel; IKA-Labortechnik) for 10 minutes and then incubated at room temperature for 1 hour with 500 units of benzonase (Merck, Darmstadt, Germany; order No. 1.01697.0001) in order to degrade the nucleic acids. Prior to cell disruption, filtration is carried out using a glass cartridge (P1). Two homogenizer runs at 1500 bar are carried out for cell disruption and for shearing the remaining genomic DNA (M-110EH microfluidizer; Microfluidics Corp.). The homogenate is centrifuged (Sorvall RC-5B, GSA rotor, 250 ml centrifuge bottles, 60 minutes, 4° C., 12 000 rpm, 23 000 g), after which the supernatant is placed on ice and the pellet is resuspended in 100 ml of sodium phosphate buffer, pH 7.5. Centrifugation and resuspension are repeated three times, with the sodium phosphate buffer comprising 1% SDS during the third repeat. After resuspension, the mixture is stirred for one hour and a final centrifugation is carried out (Sorvall RC-5B, GSA rotor, 250 ml centrifuge bottles, 60 minutes, 4° C., 12 000 rpm, 23 000 g). SDS PAGE analysis indicates that the hydrophobin is present in the supernatant after the final centrifugation (FIG. 1). The experiments show that the hydrophobin is probably present in the form of inclusion bodies in the corresponding *E. coli* cells. 50 ml of the hydrophobin-comprising supernatant are applied to a 50 ml nickel-Sepharose High Performance 17-5268-02 column (Amersham) which has been equilibrated with 50 mM Tris-Cl buffer, pH 8.0. The column is washed with 50 mM Tris-Cl buffer, pH 8.0, and the hydrophobin is then eluted with 50 mM Tris-Cl buffer, pH 8.0, comprising 200 mM imidazole. Said imidazole is removed by dialyzing the solution against 50 mM Tris-Cl buffer, pH 8.0.
FIG. 1 depicts purification of the hydrophobin of the invention:
Lane 1: Solution applied to nickel-Sepharose column (1:10 dilution)
Lane 2: Flowthrough=washing step eluate
Lanes 3-5: OD 280 peaks of the elution fractions
The hydrophobin of the invention in FIG. 1 has a molecular weight of approx. 53 kD. Some of the smaller bands represent breakdown products of said hydrophobin.

Example 9

Coating/Evaluation of Surfaces with Hydrophobin

The coating properties of hydrophobin or hydrophobin fusion protein are preferably evaluated on glass and Teflon as models for hydrophilic and hydrophobic surfaces, respectively.
Standard Coating Experiments
Glass:
   concentration of hydrophobin: 1-100 µg/mL
   incubation of glass plates overnight (temperature: 80° C.) in 50 mM sodium acetate, pH 4, +0.1% Tween 20
   after coating, washing in distilled water
   after that, incubation for 10 min at 80° C. and 1% SDS washing in distilled water.
Teflon:
   concentration: 1-100 µg/mL
   incubation of Teflon plates overnight (temperature: 80° C.) in 10 mM Tris, pH 8
   after coating, washing in distilled water
   incubation for 10 min at 80° C. and 0.1% Tween 20
   washing in distilled water
   after that, incubation for 10 min at 80° C. and 1% SDS washing in distilled water.

The samples are dried in air and the contact angle (in degrees) of a 5 μl drop of water is determined, resulting in the following values for example:

Experiment with yaad-DewA fusion protein according to Example 8 (control: without protein; yaad-dewA-his$_6$: 100 μg/ml purified fusion partner):

|  | After 1% SDS 80° C. | |
| --- | --- | --- |
|  | Teflon | Glass |
| Control | 96.8 | 30 |
| yaad | 97.4 | 38.7 |
| 100 μg/ml | 77.7 | 76.8 |
| 50 μg/ml | 85.9 | 77.9 |
| 10 μg/ml | 83.5 | 74.5 |
| 5 μg/ml | 104 | 70.3 |
| 1 μg/ml | 104.9 | 73 |

Example 10

Coating/Evaluation of Surfaces with Hydrophobin

Glass (Window Glass, Süddeutsche Glas, Mannheim, Germany):
concentration of hydrophobin: 100 μg/mL
incubation of glass plates overnight (temperature: 80° C.) in 50 mM sodium acetate, pH 4, +0.1% Tween 20
after coating, washing in distilled water
after that, incubation for 10 min at 80° C. and 1% SDS solution in distilled water
washing in distilled water.

The samples are dried in air and the contact angle (in degrees) of a 5 μl drop of water is determined.

The contact angle was measured on a Dataphysics Contact Angle System OCA 15+, Software SCA 20.2.0. (November 2002) appliance. The measurement was carried out according to the manufacturer's instructions.

Untreated glass gave a contact angle of 30±5°; a coating with a functional hydrophobin according to Example 8 (yaad-dewA-his$_6$) gave a contact angle of 75±5°.

Assignment of sequence names to DNA and polypeptide sequences in the sequence listing

| | |
| --- | --- |
| dewA DNA and polypeptide sequence | SEQ ID NO: 1 |
| dewA polypeptide sequence | SEQ ID NO: 2 |
| rodA DNA and polypeptide sequence | SEQ ID NO: 3 |
| rodA polypeptide sequence | SEQ ID NO: 4 |
| hypA DNA and polypeptide sequence | SEQ ID NO: 5 |
| hypA polypeptide sequence | SEQ ID NO: 6 |
| hypB DNA and polypeptide sequence | SEQ ID NO: 7 |
| hypB polypeptide sequence | SEQ ID NO: 8 |
| sc3 DNA and polypeptide sequence | SEQ ID NO: 9 |
| sc3 polypeptide sequence | SEQ ID NO: 10 |
| basf1 DNA and polypeptide sequence | SEQ ID NO: 11 |
| basf1 polypeptide sequence | SEQ ID NO: 12 |
| basf2 DNA and polypeptide sequence | SEQ ID NO: 13 |
| basf2 polypeptide sequence | SEQ ID NO: 14 |
| yaad DNA and polypeptide sequence | SEQ ID NO: 15 |
| yaad polypeptide sequence | SEQ ID NO: 16 |
| yaae DNA and polypeptide sequence | SEQ ID NO: 17 |
| yaae polypeptide sequence | SEQ ID NO: 18 |
| yaad-Xa-dewA-his DNA and polypeptide sequence | SEQ ID NO: 19 |
| yaad-Xa-dewA-his polypeptide sequence | SEQ ID NO: 20 |
| yaad-Xa-rodA-his DNA and polypeptide sequence | SEQ ID NO: 21 |
| yaad-Xa-rodA-his polypeptide sequence | SEQ ID NO: 22 |
| yaad-Xa-basf1-his DNA and polypeptide sequence | SEQ ID NO: 23 |
| yaad-Xa-basf1-his polypeptide sequence | SEQ ID NO: 24 |

What is claimed is:

1. A polypeptide of the general structural formula (I)

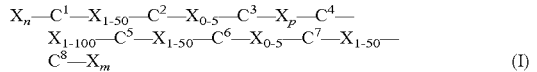 (I)

wherein each X is independently any of the 20 naturally occurring amino acids, n and m independently are numbers from 0 to 500, p is a number from 1 to 250, C is cysteine, alanine, serine, glycine, methionine or threonine wherein at least four residues designated as C are cysteine, at least one of the peptide sequences abbreviated as $X_n$ or $X_m$ or $X_p$ is a peptide sequence of at least 20 amino acids that is not naturally linked to a hydrophobin and $X_n$ or $X_m$ comprises a polypeptide sequence selected from the group consisting of SEQ ID NOs: 16 and 18, and wherein the polypeptide changes the contact angle of a drop of water on a glass surface by at least 20° after coating the glass surface with the polypeptide.

2. The polypeptide of claim 1 wherein the structural formula (I) comprises a Class I hydrophobin.

3. The polypeptide of claim 1 wherein the structural formula (I) comprises a hydrophobin selected from the group consisting of dewA, rodA, sc3, hypA, hypB, basf1, and basf2.

4. The polypeptide of claim 1 wherein the structural formula (I) comprises a sequence selected from the group consisting of SEQ ID NOs: 2, 4, 6, 8, 10, 12, and 14.

5. The polypeptide of claim 1 wherein $X_n$ or $X_m$ or $X_p$ is a $(His)_{4-10}$ sequence.

6. The polypeptide of claim 1 wherein the structural formula (I) comprises polypeptides selected from the group consisting of SEQ ID NOs: 20, 22, and 24.

7. A nucleic acid encoding the polypeptide of claim 1.

8. A method of producing a polypeptide by expressing the nucleic acid of claim 7 in a host organism and isolating the polypeptide.

9. The method of claim 8 wherein the host organism is *E. coli*.

10. A method for coating a surface with a polypeptide, the method comprising coating the surface with the polypeptide of claim 1.

* * * * *

```
                        SEQUENCE LISTING

<160> NUMBER OF SEQ ID NOS: 43

<210> SEQ ID NO 1
<211> LENGTH: 405
<212> TYPE: DNA
<213> ORGANISM: Unknown
<220> FEATURE:
<221> NAME/KEY: CDS
<222> LOCATION: (1)..(405)
<223> OTHER INFORMATION: basf-dewA

<400> SEQUENCE: 1 atg cgc ttc atc gtc tct ctc ctc gcc ttc act gcc gcg gcc acc gcg      48
Met Arg Phe Ile Val Ser Leu Leu Ala Phe Thr Ala Ala Ala Thr Ala
1               5                   10                  15 acc gcc ctc ccg gcc tct gcc gca aag aac gcg aag ctg gcc acc tcg      96
Thr Ala Leu Pro Ala Ser Ala Ala Lys Asn Ala Lys Leu Ala Thr Ser
                20                  25                  30 gcg gcc ttc gcc aag cag gct gaa ggc acc acc tgc aat gtc ggc tcg     144
Ala Ala Phe Ala Lys Gln Ala Glu Gly Thr Thr Cys Asn Val Gly Ser
            35                  40                  45 atc gct tgc tgc aac tcc ccc gct gag acc aac aac gac agt ctg ttg     192
Ile Ala Cys Cys Asn Ser Pro Ala Glu Thr Asn Asn Asp Ser Leu Leu
        50                  55                  60 agc ggt ctg ctc ggt gct ggc ctt ctc aac ggg ctc tcg ggc aac act     240
Ser Gly Leu Leu Gly Ala Gly Leu Leu Asn Gly Leu Ser Gly Asn Thr
65                  70                  75                  80
```

```
ggc agc gcc tgc gcc aag gcg agc ttg att gac cag ctg ggt ctg ctc       288
Gly Ser Ala Cys Ala Lys Ala Ser Leu Ile Asp Gln Leu Gly Leu Leu
            85                  90                  95 gct ctc gtc gac cac act gag gaa ggc ccc gtc tgc aag aac atc gtc       336
Ala Leu Val Asp His Thr Glu Glu Gly Pro Val Cys Lys Asn Ile Val
            100                 105                 110 gct tgc tgc cct gag gga acc acc aac tgt gtt gcc gtc gac aac gct       384
Ala Cys Cys Pro Glu Gly Thr Thr Asn Cys Val Ala Val Asp Asn Ala
            115                 120                 125 ggc gct ggt acc aag gct gag                                           405
Gly Ala Gly Thr Lys Ala Glu
            130                 135

<210> SEQ ID NO 2
<211> LENGTH: 135
<212> TYPE: PRT
<213> ORGANISM: Unknown
<220> FEATURE:
<223> OTHER INFORMATION: basf-dewA

<400> SEQUENCE: 2

Met Arg Phe Ile Val Ser Leu Leu Ala Phe Thr Ala Ala Ala Thr Ala
1               5                   10                  15

Thr Ala Leu Pro Ala Ser Ala Ala Lys Asn Ala Lys Leu Ala Thr Ser
            20                  25                  30

Ala Ala Phe Ala Lys Gln Ala Glu Gly Thr Thr Cys Asn Val Gly Ser
            35                  40                  45

Ile Ala Cys Cys Asn Ser Pro Ala Glu Thr Asn Asn Asp Ser Leu Leu
        50                  55                  60

Ser Gly Leu Leu Gly Ala Gly Leu Leu Asn Gly Leu Ser Gly Asn Thr
65                  70                  75                  80

Gly Ser Ala Cys Ala Lys Ala Ser Leu Ile Asp Gln Leu Gly Leu Leu
            85                  90                  95

Ala Leu Val Asp His Thr Glu Glu Gly Pro Val Cys Lys Asn Ile Val
            100                 105                 110

Ala Cys Cys Pro Glu Gly Thr Thr Asn Cys Val Ala Val Asp Asn Ala
            115                 120                 125

Gly Ala Gly Thr Lys Ala Glu
            130                 135

<210> SEQ ID NO 3
<211> LENGTH: 471
<212> TYPE: DNA
<213> ORGANISM: Unknown
<220> FEATURE:
<221> NAME/KEY: CDS
<222> LOCATION: (1)..(471)
<223> OTHER INFORMATION: basf-rodA

<400> SEQUENCE: 3 atg aag ttc tcc att gct gcc gct gtc gtt gct ttc gcc gcc tcc gtc        48
Met Lys Phe Ser Ile Ala Ala Ala Val Val Ala Phe Ala Ala Ser Val
1               5                   10                  15 gcg gcc ctc cct cct gcc cat gat tcc cag ttc gct ggc aat ggt gtt        96
Ala Ala Leu Pro Pro Ala His Asp Ser Gln Phe Ala Gly Asn Gly Val
            20                  25                  30 ggc aac aag ggc aac agc aac gtc aag ttc cct gtc ccc gaa aac gtg       144
Gly Asn Lys Gly Asn Ser Asn Val Lys Phe Pro Val Pro Glu Asn Val
            35                  40                  45 acc gtc aag cag gcc tcc gac aag tgc ggt gac cag gcc cag ctc tct       192
Thr Val Lys Gln Ala Ser Asp Lys Cys Gly Asp Gln Ala Gln Leu Ser
```

```
tgc tgc aac aag gcc acg tac gcc ggt gac acc aca acc gtt gat gag        240
Cys Cys Asn Lys Ala Thr Tyr Ala Gly Asp Thr Thr Thr Val Asp Glu
 65                  70                  75                  80 ggt ctt ctg tct ggt gcc ctc agc ggc ctc atc ggc gcc ggg tct ggt        288
Gly Leu Leu Ser Gly Ala Leu Ser Gly Leu Ile Gly Ala Gly Ser Gly
                 85                  90                  95 gcc gaa ggt ctt ggt ctc ttc gat cag tgc tcc aag ctt gat gtt gct        336
Ala Glu Gly Leu Gly Leu Phe Asp Gln Cys Ser Lys Leu Asp Val Ala
            100                 105                 110 gtc ctc att ggc atc caa gat ctt gtc aac cag aag tgc aag caa aac        384
Val Leu Ile Gly Ile Gln Asp Leu Val Asn Gln Lys Cys Lys Gln Asn
        115                 120                 125 att gcc tgc tgc cag aac tcc ccc tcc agc gcg gat ggc aac ctt att        432
Ile Ala Cys Cys Gln Asn Ser Pro Ser Ser Ala Asp Gly Asn Leu Ile
    130                 135                 140 ggt gtc ggt ctc cct tgc gtt gcc ctt ggc tcc atc ctc                    471
Gly Val Gly Leu Pro Cys Val Ala Leu Gly Ser Ile Leu
145                 150                 155
```

<210> SEQ ID NO 4
<211> LENGTH: 157
<212> TYPE: PRT
<213> ORGANISM: Unknown
<220> FEATURE:
<223> OTHER INFORMATION: basf-rodA

<400> SEQUENCE: 4

```
Met Lys Phe Ser Ile Ala Ala Val Val Ala Phe Ala Ala Ser Val
 1               5                  10                  15

Ala Ala Leu Pro Pro Ala His Asp Ser Gln Phe Ala Gly Asn Gly Val
            20                  25                  30

Gly Asn Lys Gly Asn Ser Asn Val Lys Phe Pro Val Pro Glu Asn Val
        35                  40                  45

Thr Val Lys Gln Ala Ser Asp Lys Cys Gly Asp Gln Ala Gln Leu Ser
    50                  55                  60

Cys Cys Asn Lys Ala Thr Tyr Ala Gly Asp Thr Thr Thr Val Asp Glu
 65                  70                  75                  80

Gly Leu Leu Ser Gly Ala Leu Ser Gly Leu Ile Gly Ala Gly Ser Gly
                 85                  90                  95

Ala Glu Gly Leu Gly Leu Phe Asp Gln Cys Ser Lys Leu Asp Val Ala
            100                 105                 110

Val Leu Ile Gly Ile Gln Asp Leu Val Asn Gln Lys Cys Lys Gln Asn
        115                 120                 125

Ile Ala Cys Cys Gln Asn Ser Pro Ser Ser Ala Asp Gly Asn Leu Ile
    130                 135                 140

Gly Val Gly Leu Pro Cys Val Ala Leu Gly Ser Ile Leu
145                 150                 155
```

<210> SEQ ID NO 5
<211> LENGTH: 336
<212> TYPE: DNA
<213> ORGANISM: Unknown
<220> FEATURE:
<221> NAME/KEY: CDS
<222> LOCATION: (1)..(336)
<223> OTHER INFORMATION: basf-HypA

<400> SEQUENCE: 5

```
atg atc tct cgc gtc ctt gtc gct gct ctc gtc gct ctc ccc gct ctt        48
Met Ile Ser Arg Val Leu Val Ala Ala Leu Val Ala Leu Pro Ala Leu
```

```
gtt act gca act cct gct ccc gga aag cct aaa gcc agc agt cag tgc        96
Val Thr Ala Thr Pro Ala Pro Gly Lys Pro Lys Ala Ser Ser Gln Cys
             20                  25                  30 gac gtc ggt gaa atc cat tgc tgt gac act cag cag act ccc gac cac       144
Asp Val Gly Glu Ile His Cys Cys Asp Thr Gln Gln Thr Pro Asp His
             35                  40                  45 acc agc gcc gcc gcg tct ggt ttg ctt ggt gtt ccc atc aac ctt ggt       192
Thr Ser Ala Ala Ala Ser Gly Leu Leu Gly Val Pro Ile Asn Leu Gly
 50                  55                  60 gct ttc ctc ggt ttc gac tgt acc ccc att tcc gtc ctt ggc gtc ggt       240
Ala Phe Leu Gly Phe Asp Cys Thr Pro Ile Ser Val Leu Gly Val Gly
 65                  70                  75                  80 ggc aac aac tgt gct gct cag cct gtc tgc tgc aca gga aat caa ttc       288
Gly Asn Asn Cys Ala Ala Gln Pro Val Cys Cys Thr Gly Asn Gln Phe
                 85                  90                  95 acc gca ttg att aac gct ctt gac tgc tct cct gtc aat gtc aac ctc       336
Thr Ala Leu Ile Asn Ala Leu Asp Cys Ser Pro Val Asn Val Asn Leu
            100                 105                 110
```

<210> SEQ ID NO 6
<211> LENGTH: 112
<212> TYPE: PRT
<213> ORGANISM: Unknown
<220> FEATURE:
<223> OTHER INFORMATION: basf-HypA

<400> SEQUENCE: 6

Met Ile Ser Arg Val Leu Val Ala Ala Leu Val Ala Leu Pro Ala Leu
 1               5                  10                  15

Val Thr Ala Thr Pro Ala Pro Gly Lys Pro Lys Ala Ser Ser Gln Cys
             20                  25                  30

Asp Val Gly Glu Ile His Cys Cys Asp Thr Gln Gln Thr Pro Asp His
         35                      40                  45

Thr Ser Ala Ala Ala Ser Gly Leu Leu Gly Val Pro Ile Asn Leu Gly
 50                  55                  60

Ala Phe Leu Gly Phe Asp Cys Thr Pro Ile Ser Val Leu Gly Val Gly
 65                  70                  75                  80

Gly Asn Asn Cys Ala Ala Gln Pro Val Cys Cys Thr Gly Asn Gln Phe
                 85                  90                  95

Thr Ala Leu Ile Asn Ala Leu Asp Cys Ser Pro Val Asn Val Asn Leu
            100                 105                 110

<210> SEQ ID NO 7
<211> LENGTH: 357
<212> TYPE: DNA
<213> ORGANISM: Unknown
<220> FEATURE:
<221> NAME/KEY: CDS
<222> LOCATION: (1)..(357)
<223> OTHER INFORMATION: basf-HypB

<400> SEQUENCE: 7

```
atg gtc agc acg ttc atc act gtc gca aag acc ctt ctc gtc gcg ctc        48
Met Val Ser Thr Phe Ile Thr Val Ala Lys Thr Leu Leu Val Ala Leu
 1               5                  10                  15 ctc ttc gtc aat atc aat atc gtc gtt ggt act gca act acc ggc aag        96
Leu Phe Val Asn Ile Asn Ile Val Val Gly Thr Ala Thr Thr Gly Lys
             20                  25                  30 cat tgt agc acc ggt cct atc gag tgt tgc aag cag gtc atg gat tct       144
His Cys Ser Thr Gly Pro Ile Glu Cys Cys Lys Gln Val Met Asp Ser
             35                  40                  45
```

```
aag agc cct cag gct acg gag ctt ctt acg aag aat ggc ctt ggc ctg    192
Lys Ser Pro Gln Ala Thr Glu Leu Leu Thr Lys Asn Gly Leu Gly Leu
     50                  55                  60 ggt gtc ctt gct ggc gtg aag ggt ctt gtt ggc gcg aat tgc agc cct    240
Gly Val Leu Ala Gly Val Lys Gly Leu Val Gly Ala Asn Cys Ser Pro
 65                  70                  75                  80 atc acg gca att ggt att ggc tcc ggc agc caa tgc tct ggc cag acc    288
Ile Thr Ala Ile Gly Ile Gly Ser Gly Ser Gln Cys Ser Gly Gln Thr
                 85                  90                  95 gtt tgc tgc cag aat aat aat ttc aac ggt gtt gtc gct att ggt tgc    336
Val Cys Cys Gln Asn Asn Asn Phe Asn Gly Val Val Ala Ile Gly Cys
            100                 105                 110 act ccc att aat gcc aat gtg                                        357
Thr Pro Ile Asn Ala Asn Val
       115
```

<210> SEQ ID NO 8
<211> LENGTH: 119
<212> TYPE: PRT
<213> ORGANISM: Unknown
<220> FEATURE:
<223> OTHER INFORMATION: basf-HypB

<400> SEQUENCE: 8

```
Met Val Ser Thr Phe Ile Thr Val Ala Lys Thr Leu Leu Val Ala Leu
 1               5                  10                  15

Leu Phe Val Asn Ile Asn Ile Val Val Gly Thr Ala Thr Thr Gly Lys
                20                  25                  30

His Cys Ser Thr Gly Pro Ile Glu Cys Cys Lys Gln Val Met Asp Ser
             35                  40                  45

Lys Ser Pro Gln Ala Thr Glu Leu Leu Thr Lys Asn Gly Leu Gly Leu
         50                  55                  60

Gly Val Leu Ala Gly Val Lys Gly Leu Val Gly Ala Asn Cys Ser Pro
 65                  70                  75                  80

Ile Thr Ala Ile Gly Ile Gly Ser Gly Ser Gln Cys Ser Gly Gln Thr
                 85                  90                  95

Val Cys Cys Gln Asn Asn Asn Phe Asn Gly Val Val Ala Ile Gly Cys
            100                 105                 110

Thr Pro Ile Asn Ala Asn Val
        115
```

<210> SEQ ID NO 9
<211> LENGTH: 408
<212> TYPE: DNA
<213> ORGANISM: Unknown
<220> FEATURE:
<221> NAME/KEY: CDS
<222> LOCATION: (1)..(408)
<223> OTHER INFORMATION: basf-sc3

<400> SEQUENCE: 9

```
atg ttc gcc cgt ctc ccc gtc gtg ttc ctc tac gcc ttc gtc gcg ttc    48
Met Phe Ala Arg Leu Pro Val Val Phe Leu Tyr Ala Phe Val Ala Phe
 1               5                  10                  15 ggc gcc ctc gtc gct gcc ctc cca ggt ggc cac ccg ggc acg acc acg    96
Gly Ala Leu Val Ala Ala Leu Pro Gly Gly His Pro Gly Thr Thr Thr
                20                  25                  30 ccg ccg gtt acg acg acg gtg acg gtg acc acg ccg ccc tcg acg acg    144
Pro Pro Val Thr Thr Thr Val Thr Val Thr Thr Pro Pro Ser Thr Thr
             35                  40                  45 acc atc gcc gcc ggt ggc acg tgt act acg ggg tcg ctc tct tgc tgc    192
```

```
Thr Ile Ala Ala Gly Gly Thr Cys Thr Thr Gly Ser Leu Ser Cys Cys
    50                  55                  60 aac cag gtt caa tcg gcg agc agc agc cct gtt acc gcc ctc ctc ggc     240
Asn Gln Val Gln Ser Ala Ser Ser Ser Pro Val Thr Ala Leu Leu Gly
 65                  70                  75                  80 ctg ctc ggc att gtc ctc agc gac ctc aac gtt ctc gtt ggc atc agc     288
Leu Leu Gly Ile Val Leu Ser Asp Leu Asn Val Leu Val Gly Ile Ser
                 85                  90                  95 tgc tct ccc ctc act gtc atc ggt gtc gga ggc agc ggc tgt tcg gcg     336
Cys Ser Pro Leu Thr Val Ile Gly Val Gly Gly Ser Gly Cys Ser Ala
            100                 105                 110 cag acc gtc tgc tgc gaa aac acc caa ttc aac ggg ctg atc aac atc     384
Gln Thr Val Cys Cys Glu Asn Thr Gln Phe Asn Gly Leu Ile Asn Ile
        115                 120                 125 ggt tgc acc ccc atc aac atc ctc                                     408
Gly Cys Thr Pro Ile Asn Ile Leu
    130                 135

<210> SEQ ID NO 10
<211> LENGTH: 136
<212> TYPE: PRT
<213> ORGANISM: basf-sc3
<220> FEATURE:
<223> OTHER INFORMATION: basf-sc3

<400> SEQUENCE: 10

Met Phe Ala Arg Leu Pro Val Val Phe Leu Tyr Ala Phe Val Ala Phe
 1               5                  10                  15

Gly Ala Leu Val Ala Ala Leu Pro Gly Gly His Pro Gly Thr Thr Thr
                20                  25                  30

Pro Pro Val Thr Thr Thr Val Thr Val Thr Thr Pro Pro Ser Thr Thr
            35                  40                  45

Thr Ile Ala Ala Gly Gly Thr Cys Thr Thr Gly Ser Leu Ser Cys Cys
    50                  55                  60

Asn Gln Val Gln Ser Ala Ser Ser Ser Pro Val Thr Ala Leu Leu Gly
 65                  70                  75                  80

Leu Leu Gly Ile Val Leu Ser Asp Leu Asn Val Leu Val Gly Ile Ser
                 85                  90                  95

Cys Ser Pro Leu Thr Val Ile Gly Val Gly Gly Ser Gly Cys Ser Ala
            100                 105                 110

Gln Thr Val Cys Cys Glu Asn Thr Gln Phe Asn Gly Leu Ile Asn Ile
        115                 120                 125

Gly Cys Thr Pro Ile Asn Ile Leu
    130                 135

<210> SEQ ID NO 11
<211> LENGTH: 483
<212> TYPE: DNA
<213> ORGANISM: Unknown
<220> FEATURE:
<221> NAME/KEY: CDS
<222> LOCATION: (1)..(483)
<223> OTHER INFORMATION: basf-BASF1

<400> SEQUENCE: 11 atg aag ttc tcc gtc tcc gcc gcc gtc ctc gcc ttc gcc gcc tcc gtc      48
Met Lys Phe Ser Val Ser Ala Ala Val Leu Ala Phe Ala Ala Ser Val
 1               5                  10                  15 gcc gcc ctc cct cag cac gac tcc gcc gcc ggc aac ggc aac ggc gtc      96
Ala Ala Leu Pro Gln His Asp Ser Ala Ala Gly Asn Gly Asn Gly Val
                20                  25                  30
```

```
ggc aac aag ttc cct gtc cct gac gac gtc acc gtc aag cag gcc acc    144
Gly Asn Lys Phe Pro Val Pro Asp Asp Val Thr Val Lys Gln Ala Thr
         35                  40                  45 gac aag tgc ggc gac cag gcc cag ctc tcc tgc tgc aac aag gcc acc    192
Asp Lys Cys Gly Asp Gln Ala Gln Leu Ser Cys Cys Asn Lys Ala Thr
 50                  55                  60 tac gcc ggc gac gtc ctc acc gac atc gac gag ggc atc ctc gcc ggc    240
Tyr Ala Gly Asp Val Leu Thr Asp Ile Asp Glu Gly Ile Leu Ala Gly
 65                  70                  75                  80 ctc ctc aag aac ctc atc ggc ggc tcc ggc tcc gag ggc ctc ggc        288
Leu Leu Lys Asn Leu Ile Gly Gly Ser Gly Ser Glu Gly Leu Gly
                 85                  90                  95 ctc ttc gac cag tgc gtc aag ctc gac ctc cag atc tcc gtc atc ggc    336
Leu Phe Asp Gln Cys Val Lys Leu Asp Leu Gln Ile Ser Val Ile Gly
                100                 105                 110 atc cct atc cag gac ctc ctc aac cag gtc aac aag cag tgc aag cag    384
Ile Pro Ile Gln Asp Leu Leu Asn Gln Val Asn Lys Gln Cys Lys Gln
                115                 120                 125 aac atc gcc tgc tgc cag aac tcc cct tcc gac gcc acc ggc tcc ctc    432
Asn Ile Ala Cys Cys Gln Asn Ser Pro Ser Asp Ala Thr Gly Ser Leu
130                 135                 140 gtc aac ctc ggc ctc ggc aac cct tgc atc cct gtc tcc ctc ctc cat    480
Val Asn Leu Gly Leu Gly Asn Pro Cys Ile Pro Val Ser Leu Leu His
145                 150                 155                 160 atg                                                                483
Met

<210> SEQ ID NO 12
<211> LENGTH: 161
<212> TYPE: PRT
<213> ORGANISM: Unknown
<220> FEATURE:
<223> OTHER INFORMATION: basf-BASF1

<400> SEQUENCE: 12

Met Lys Phe Ser Val Ser Ala Ala Val Leu Ala Phe Ala Ala Ser Val
 1               5                  10                  15

Ala Ala Leu Pro Gln His Asp Ser Ala Ala Gly Asn Gly Asn Gly Val
                 20                  25                  30

Gly Asn Lys Phe Pro Val Pro Asp Asp Val Thr Val Lys Gln Ala Thr
         35                  40                  45

Asp Lys Cys Gly Asp Gln Ala Gln Leu Ser Cys Cys Asn Lys Ala Thr
 50                  55                  60

Tyr Ala Gly Asp Val Leu Thr Asp Ile Asp Glu Gly Ile Leu Ala Gly
 65                  70                  75                  80

Leu Leu Lys Asn Leu Ile Gly Gly Ser Gly Ser Glu Gly Leu Gly
                 85                  90                  95

Leu Phe Asp Gln Cys Val Lys Leu Asp Leu Gln Ile Ser Val Ile Gly
                100                 105                 110

Ile Pro Ile Gln Asp Leu Leu Asn Gln Val Asn Lys Gln Cys Lys Gln
                115                 120                 125

Asn Ile Ala Cys Cys Gln Asn Ser Pro Ser Asp Ala Thr Gly Ser Leu
    130                 135                 140

Val Asn Leu Gly Leu Gly Asn Pro Cys Ile Pro Val Ser Leu Leu His
145                 150                 155                 160

Met

<210> SEQ ID NO 13
<211> LENGTH: 465
```

```
<212> TYPE: DNA
<213> ORGANISM: Unknown
<220> FEATURE:
<221> NAME/KEY: CDS
<222> LOCATION: (1)..(465)
<223> OTHER INFORMATION: basf-BASF2

<400> SEQUENCE: 13 atg aag ttc tcc gtc tcc gcc gcc gtc ctc gcc ttc gcc gcc tcc gtc      48
Met Lys Phe Ser Val Ser Ala Ala Val Leu Ala Phe Ala Ala Ser Val
1               5                   10                  15 gcc gcc ctc cct cag cac gac tcc gcc gcc ggc aac ggc aac ggc gtc      96
Ala Ala Leu Pro Gln His Asp Ser Ala Ala Gly Asn Gly Asn Gly Val
                20                  25                  30 ggc aac aag ttc cct gtc cct gac gac gtc acc gtc aag cag gcc acc     144
Gly Asn Lys Phe Pro Val Pro Asp Asp Val Thr Val Lys Gln Ala Thr
            35                  40                  45 gac aag tgc ggc gac cag gcc cag ctc tcc tgc tgc aac aag gcc acc     192
Asp Lys Cys Gly Asp Gln Ala Gln Leu Ser Cys Cys Asn Lys Ala Thr
        50                  55                  60 tac gcc ggc gac gtc acc gac atc gac gag ggc atc ctc gcc ggc ctc     240
Tyr Ala Gly Asp Val Thr Asp Ile Asp Glu Gly Ile Leu Ala Gly Leu
65                  70                  75                  80 ctc aag aac ctc atc ggc ggc ggc tcc ggc tcc gag ggc ctc ggc ctc     288
Leu Lys Asn Leu Ile Gly Gly Gly Ser Gly Ser Glu Gly Leu Gly Leu
                85                  90                  95 ttc gac cag tgc gtc aag ctc gac ctc cag atc tcc gtc atc ggc atc     336
Phe Asp Gln Cys Val Lys Leu Asp Leu Gln Ile Ser Val Ile Gly Ile
            100                 105                 110 cct atc cag gac ctc ctc aac cag cag tgc aag cag aac atc gcc tgc     384
Pro Ile Gln Asp Leu Leu Asn Gln Gln Cys Lys Gln Asn Ile Ala Cys
        115                 120                 125 tgc cag aac tcc cct tcc gac gcc acc ggc tcc ctc gtc aac ctc ggc     432
Cys Gln Asn Ser Pro Ser Asp Ala Thr Gly Ser Leu Val Asn Leu Gly
    130                 135                 140 aac cct tgc atc cct gtc tcc ctc ctc cat atg                         465
Asn Pro Cys Ile Pro Val Ser Leu Leu His Met
145                 150                 155

<210> SEQ ID NO 14
<211> LENGTH: 155
<212> TYPE: PRT
<213> ORGANISM: Unknown
<220> FEATURE:
<223> OTHER INFORMATION: basf-BASF2

<400> SEQUENCE: 14

Met Lys Phe Ser Val Ser Ala Ala Val Leu Ala Phe Ala Ala Ser Val
1               5                   10                  15

Ala Ala Leu Pro Gln His Asp Ser Ala Ala Gly Asn Gly Asn Gly Val
                20                  25                  30

Gly Asn Lys Phe Pro Val Pro Asp Asp Val Thr Val Lys Gln Ala Thr
            35                  40                  45

Asp Lys Cys Gly Asp Gln Ala Gln Leu Ser Cys Cys Asn Lys Ala Thr
        50                  55                  60

Tyr Ala Gly Asp Val Thr Asp Ile Asp Glu Gly Ile Leu Ala Gly Leu
65                  70                  75                  80

Leu Lys Asn Leu Ile Gly Gly Gly Ser Gly Ser Glu Gly Leu Gly Leu
                85                  90                  95

Phe Asp Gln Cys Val Lys Leu Asp Leu Gln Ile Ser Val Ile Gly Ile
            100                 105                 110
```

```
Pro Ile Gln Asp Leu Leu Asn Gln Gln Cys Lys Gln Asn Ile Ala Cys
            115                 120                 125

Cys Gln Asn Ser Pro Ser Asp Ala Thr Gly Ser Leu Val Asn Leu Gly
        130                 135                 140

Asn Pro Cys Ile Pro Val Ser Leu Leu His Met
145                 150                 155

<210> SEQ ID NO 15
<211> LENGTH: 882
<212> TYPE: DNA
<213> ORGANISM: Unknown
<220> FEATURE:
<221> NAME/KEY: CDS
<222> LOCATION: (1)..(882)
<223> OTHER INFORMATION: basf-yaad

<400> SEQUENCE: 15 atg gct caa aca ggt act gaa cgt gta aaa cgc gga atg gca gaa atg      48
Met Ala Gln Thr Gly Thr Glu Arg Val Lys Arg Gly Met Ala Glu Met
1               5                   10                  15 caa aaa ggc ggc gtc atc atg gac gtc atc aat gca gaa caa gcg aaa      96
Gln Lys Gly Gly Val Ile Met Asp Val Ile Asn Ala Glu Gln Ala Lys
            20                  25                  30 atc gct gaa gaa gct gga gct gtc gct gta atg gcg cta gaa cgt gtg     144
Ile Ala Glu Glu Ala Gly Ala Val Ala Val Met Ala Leu Glu Arg Val
        35                  40                  45 cca gca gat att cgc gcg gct gga gga gtt gcc cgt atg gct gac cct     192
Pro Ala Asp Ile Arg Ala Ala Gly Gly Val Ala Arg Met Ala Asp Pro
    50                  55                  60 aca atc gtg gaa gaa gta atg aat gca gta tct atc ccg gta atg gca     240
Thr Ile Val Glu Glu Val Met Asn Ala Val Ser Ile Pro Val Met Ala
65                  70                  75                  80 aaa gcg cgt atc gga cat att gtt gaa gcg cgt gtg ctt gaa gct atg     288
Lys Ala Arg Ile Gly His Ile Val Glu Ala Arg Val Leu Glu Ala Met
                85                  90                  95 ggt gtt gac tat att gat gaa agt gaa gtt ctg acg ccg gct gac gaa     336
Gly Val Asp Tyr Ile Asp Glu Ser Glu Val Leu Thr Pro Ala Asp Glu
            100                 105                 110 gaa ttt cat tta aat aaa aat gaa tac aca gtt cct ttt gtc tgt ggc     384
Glu Phe His Leu Asn Lys Asn Glu Tyr Thr Val Pro Phe Val Cys Gly
        115                 120                 125 tgc cgt gat ctt ggt gaa gca aca cgc cgt att gcg gaa ggt gct tct     432
Cys Arg Asp Leu Gly Glu Ala Thr Arg Arg Ile Ala Glu Gly Ala Ser
    130                 135                 140 atg ctt cgc aca aaa ggt gag cct gga aca ggt aat att gtt gag gct     480
Met Leu Arg Thr Lys Gly Glu Pro Gly Thr Gly Asn Ile Val Glu Ala
145                 150                 155                 160 gtt cgc cat atg cgt aaa gtt aac gct caa gtg cgc aaa gta gtt gcg     528
Val Arg His Met Arg Lys Val Asn Ala Gln Val Arg Lys Val Val Ala
                165                 170                 175 atg agt gag gat gag cta atg aca gaa gcg aaa aac cta ggt gct cct     576
Met Ser Glu Asp Glu Leu Met Thr Glu Ala Lys Asn Leu Gly Ala Pro
            180                 185                 190 tac gag ctt ctt ctt caa att aaa aaa gac ggc aag ctt cct gtc gtt     624
Tyr Glu Leu Leu Leu Gln Ile Lys Lys Asp Gly Lys Leu Pro Val Val
        195                 200                 205 aac ttt gcc gct ggc ggc gta gca act cca gct gat gct gct ctc atg     672
Asn Phe Ala Ala Gly Gly Val Ala Thr Pro Ala Asp Ala Ala Leu Met
    210                 215                 220 atg cag ctt ggt gct gac gga gta ttt gtt ggt tct ggt att ttt aaa     720
Met Gln Leu Gly Ala Asp Gly Val Phe Val Gly Ser Gly Ile Phe Lys
225                 230                 235                 240
```

```
tca gac aac cct gct aaa ttt gcg aaa gca att gtg gaa gca aca act      768
Ser Asp Asn Pro Ala Lys Phe Ala Lys Ala Ile Val Glu Ala Thr Thr
            245                 250                 255 cac ttt act gat tac aaa tta atc gct gag ttg tca aaa gag ctt ggt      816
His Phe Thr Asp Tyr Lys Leu Ile Ala Glu Leu Ser Lys Glu Leu Gly
        260                 265                 270 act gca atg aaa ggg att gaa atc tca aac tta ctt cca gaa cag cgt      864
Thr Ala Met Lys Gly Ile Glu Ile Ser Asn Leu Leu Pro Glu Gln Arg
        275                 280                 285 atg caa gaa cgc ggc tgg                                              882
Met Gln Glu Arg Gly Trp
    290

<210> SEQ ID NO 16
<211> LENGTH: 294
<212> TYPE: PRT
<213> ORGANISM: basf-yaad
<220> FEATURE:
<223> OTHER INFORMATION: basf-yaad

<400> SEQUENCE: 16
```

Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60

Thr Ile Val Glu Glu Val Met Asn Ala Val Ser Ile Pro Val Met Ala
65                  70                  75                  80

Lys Ala Arg Ile Gly His Ile Val Glu Ala Arg Val Leu Glu Ala Met
                85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
        195                 200                 205

Asn Phe Ala Ala Gly Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
        275                 280                 285

Met Gln Glu Arg Gly Trp
    290

<210> SEQ ID NO 17
<211> LENGTH: 591
<212> TYPE: DNA
<213> ORGANISM: Unknown
<220> FEATURE:
<221> NAME/KEY: CDS
<222> LOCATION: (1)..(591)
<223> OTHER INFORMATION: basf-yaae

<400> SEQUENCE: 17

```
atg gga tta aca ata ggt gta cta gga ctt caa gga gca gtt aga gag      48
Met Gly Leu Thr Ile Gly Val Leu Gly Leu Gln Gly Ala Val Arg Glu
1               5                   10                  15 cac atc cat gcg att gaa gca tgc ggc gcg gct ggt ctt gtc gta aaa      96
His Ile His Ala Ile Glu Ala Cys Gly Ala Ala Gly Leu Val Val Lys
                20                  25                  30 cgt ccg gag cag ctg aac gaa gtt gac ggg ttg att ttg ccg ggc ggt     144
Arg Pro Glu Gln Leu Asn Glu Val Asp Gly Leu Ile Leu Pro Gly Gly
            35                  40                  45 gag agc acg acg atg cgc cgt ttg atc gat acg tat caa ttc atg gag     192
Glu Ser Thr Thr Met Arg Arg Leu Ile Asp Thr Tyr Gln Phe Met Glu
        50                  55                  60 ccg ctt cgt gaa ttc gct gct cag ggc aaa ccg atg ttt gga aca tgt     240
Pro Leu Arg Glu Phe Ala Ala Gln Gly Lys Pro Met Phe Gly Thr Cys
65                  70                  75                  80 gcc gga tta att ata tta gca aaa gaa att gcc ggt tca gat aat cct     288
Ala Gly Leu Ile Ile Leu Ala Lys Glu Ile Ala Gly Ser Asp Asn Pro
                85                  90                  95 cat tta ggt ctt ctg aat gtg gtt gta gaa cgt aat tca ttt ggc cgg     336
His Leu Gly Leu Leu Asn Val Val Val Glu Arg Asn Ser Phe Gly Arg
                100                 105                 110 cag gtt gac agc ttt gaa gct gat tta aca att aaa ggc ttg gac gag     384
Gln Val Asp Ser Phe Glu Ala Asp Leu Thr Ile Lys Gly Leu Asp Glu
            115                 120                 125 cct ttt act ggg gta ttc atc cgt gct ccg cat att tta gaa gct ggt     432
Pro Phe Thr Gly Val Phe Ile Arg Ala Pro His Ile Leu Glu Ala Gly
        130                 135                 140 gaa aat gtt gaa gtt cta tcg gag cat aat ggt cgt att gta gcc gcg     480
Glu Asn Val Glu Val Leu Ser Glu His Asn Gly Arg Ile Val Ala Ala
145                 150                 155                 160 aaa cag ggg caa ttc ctt ggc tgc tca ttc cat ccg gag ctg aca gaa     528
Lys Gln Gly Gln Phe Leu Gly Cys Ser Phe His Pro Glu Leu Thr Glu
                165                 170                 175 gat cac cga gtg acg cag ctg ttt gtt gaa atg gtt gag gaa tat aag     576
Asp His Arg Val Thr Gln Leu Phe Val Glu Met Val Glu Glu Tyr Lys
            180                 185                 190 caa aag gca ctt gta                                                 591
Gln Lys Ala Leu Val
        195
```

<210> SEQ ID NO 18
<211> LENGTH: 197
<212> TYPE: PRT
<213> ORGANISM: Unknown
<220> FEATURE:
<223> OTHER INFORMATION: basf-yaae

<400> SEQUENCE: 18

```
Met Gly Leu Thr Ile Gly Val Leu Gly Leu Gln Gly Ala Val Arg Glu
1               5                   10                  15
```

```
His Ile His Ala Ile Glu Ala Cys Gly Ala Ala Gly Leu Val Val Lys
             20                  25                  30

Arg Pro Glu Gln Leu Asn Glu Val Asp Gly Leu Ile Leu Pro Gly Gly
         35                  40                  45

Glu Ser Thr Thr Met Arg Arg Leu Ile Asp Thr Tyr Gln Phe Met Glu
 50                  55                  60

Pro Leu Arg Glu Phe Ala Ala Gln Gly Lys Pro Met Phe Gly Thr Cys
 65                  70                  75                  80

Ala Gly Leu Ile Ile Leu Ala Lys Glu Ile Ala Gly Ser Asp Asn Pro
                 85                  90                  95

His Leu Gly Leu Leu Asn Val Val Glu Arg Asn Ser Phe Gly Arg
            100                 105                 110

Gln Val Asp Ser Phe Glu Ala Asp Leu Thr Ile Lys Gly Leu Asp Glu
            115                 120                 125

Pro Phe Thr Gly Val Phe Ile Arg Ala Pro His Ile Leu Glu Ala Gly
        130                 135                 140

Glu Asn Val Glu Val Leu Ser Glu His Asn Gly Arg Ile Val Ala Ala
145                 150                 155                 160

Lys Gln Gly Gln Phe Leu Gly Cys Ser Phe His Pro Glu Leu Thr Glu
                165                 170                 175

Asp His Arg Val Thr Gln Leu Phe Val Glu Met Val Gly Glu Tyr Lys
            180                 185                 190

Gln Lys Ala Leu Val
        195
```

<210> SEQ ID NO 19
<211> LENGTH: 1329
<212> TYPE: DNA
<213> ORGANISM: Unknown
<220> FEATURE:
<221> NAME/KEY: CDS
<222> LOCATION: (1)..(1329)
<223> OTHER INFORMATION: basf-yaad-Xa-dewA-his

<400> SEQUENCE: 19

```
atg gct caa aca ggt act gaa cgt gta aaa cgc gga atg gca gaa atg       48
Met Ala Gln Thr Gly Thr Glu Arg Val Lys Arg Gly Met Ala Glu Met
 1               5                  10                  15 caa aaa ggc ggc gtc atc atg gac gtc atc aat gcg gaa caa gcg aaa       96
Gln Lys Gly Gly Val Ile Met Asp Val Ile Asn Ala Glu Gln Ala Lys
             20                  25                  30 atc gct gaa gaa gct gga gct gtc gct gta atg gcg cta gaa cgt gtg      144
Ile Ala Glu Glu Ala Gly Ala Val Ala Val Met Ala Leu Glu Arg Val
         35                  40                  45 cca gca gat att cgc gcg gct gga gga gtt gcc cgt atg gct gac cct      192
Pro Ala Asp Ile Arg Ala Ala Gly Gly Val Ala Arg Met Ala Asp Pro
     50                  55                  60 aca atc gtg gaa gaa gta atg aat gca gta tct atc ccg gta atg gca      240
Thr Ile Val Glu Glu Val Met Asn Ala Val Ser Ile Pro Val Met Ala
 65                  70                  75                  80 aaa gcg cgt atc gga cat att gtt gaa gcg cgt gtg ctt gaa gct atg      288
Lys Ala Arg Ile Gly His Ile Val Glu Ala Arg Val Leu Glu Ala Met
                 85                  90                  95 ggt gtt gac tat att gat gaa agt gaa gtt ctg acg ccg gct gac gaa      336
Gly Val Asp Tyr Ile Asp Glu Ser Glu Val Leu Thr Pro Ala Asp Glu
            100                 105                 110 gaa ttt cat tta aat aaa aat gaa tac aca gtt cct ttt gtc tgt ggc      384
Glu Phe His Leu Asn Lys Asn Glu Tyr Thr Val Pro Phe Val Cys Gly
        115                 120                 125
```

```
tgc cgt gat ctt ggt gaa gca aca cgc cgt att gcg gaa ggt gct tct        432
Cys Arg Asp Leu Gly Glu Ala Thr Arg Arg Ile Ala Glu Gly Ala Ser
    130                 135                 140 atg ctt cgc aca aaa ggt gag cct gga aca ggt aat att gtt gag gct        480
Met Leu Arg Thr Lys Gly Glu Pro Gly Thr Gly Asn Ile Val Glu Ala
145                 150                 155                 160 gtt cgc cat atg cgt aaa gtt aac gct caa gtg cgc aaa gta gtt gcg        528
Val Arg His Met Arg Lys Val Asn Ala Gln Val Arg Lys Val Val Ala
                165                 170                 175 atg agt gag gat gag cta atg aca gaa gcg aaa aac cta ggt gct cct        576
Met Ser Glu Asp Glu Leu Met Thr Glu Ala Lys Asn Leu Gly Ala Pro
            180                 185                 190 tac gag ctt ctt ctt caa att aaa aaa gac ggc aag ctt cct gtc gtt        624
Tyr Glu Leu Leu Leu Gln Ile Lys Lys Asp Gly Lys Leu Pro Val Val
        195                 200                 205 aac ttt gcc gct ggc ggc gta gca act cca gct gat gct gct ctc atg        672
Asn Phe Ala Ala Gly Gly Val Ala Thr Pro Ala Asp Ala Ala Leu Met
    210                 215                 220 atg cag ctt ggt gct gac gga gta ttt gtt ggt tct ggt att ttt aaa        720
Met Gln Leu Gly Ala Asp Gly Val Phe Val Gly Ser Gly Ile Phe Lys
225                 230                 235                 240 tca gac aac cct gct aaa ttt gcg aaa gca att gtg gaa gca aca act        768
Ser Asp Asn Pro Ala Lys Phe Ala Lys Ala Ile Val Glu Ala Thr Thr
                245                 250                 255 cac ttt act gat tac aaa tta atc gct gag ttg tca aaa gag ctt ggt        816
His Phe Thr Asp Tyr Lys Leu Ile Ala Glu Leu Ser Lys Glu Leu Gly
            260                 265                 270 act gca atg aaa ggg att gaa atc tca aac tta ctt cca gaa cag cgt        864
Thr Ala Met Lys Gly Ile Glu Ile Ser Asn Leu Leu Pro Glu Gln Arg
        275                 280                 285 atg caa gaa cgc ggc tgg aga tcc att gaa ggc cgc atg cgc ttc atc        912
Met Gln Glu Arg Gly Trp Arg Ser Ile Glu Gly Arg Met Arg Phe Ile
    290                 295                 300 gtc tct ctc ctc gcc ttc act gcc gcg gcc acc gcg acc gcc ctc ccg        960
Val Ser Leu Leu Ala Phe Thr Ala Ala Ala Thr Ala Thr Ala Leu Pro
305                 310                 315                 320 gcc tct gcc gca aag aac gcg aag ctg gcc acc tcg gcg gcc ttc gcc       1008
Ala Ser Ala Ala Lys Asn Ala Lys Leu Ala Thr Ser Ala Ala Phe Ala
                325                 330                 335 aag cag gct gaa ggc acc acc tgc aat gtc ggc tcg atc gct tgc tgc       1056
Lys Gln Ala Glu Gly Thr Thr Cys Asn Val Gly Ser Ile Ala Cys Cys
            340                 345                 350 aac tcc ccc gct gag acc aac aac gac agt ctg ttg agc ggt ctg ctc       1104
Asn Ser Pro Ala Glu Thr Asn Asn Asp Ser Leu Leu Ser Gly Leu Leu
        355                 360                 365 ggt gct ggc ctt ctc aac ggg ctc tcg ggc aac act ggc agc gcc tgc       1152
Gly Ala Gly Leu Leu Asn Gly Leu Ser Gly Asn Thr Gly Ser Ala Cys
    370                 375                 380 gcc aag gcg agc ttg att gac cag ctg ggt ctg ctc gct ctc gtc gac       1200
Ala Lys Ala Ser Leu Ile Asp Gln Leu Gly Leu Leu Ala Leu Val Asp
385                 390                 395                 400 cac act gag gaa ggc ccc gtc tgc aag aac atc gtc gct tgc tgc cct       1248
His Thr Glu Glu Gly Pro Val Cys Lys Asn Ile Val Ala Cys Cys Pro
                405                 410                 415 gag gga acc acc aac tgt gtt gcc gtc gac aac gct ggc gct ggt acc       1296
Glu Gly Thr Thr Asn Cys Val Ala Val Asp Asn Ala Gly Ala Gly Thr
            420                 425                 430 aag gct gag gga tct cat cac cat cac cat cac                           1329
Lys Ala Glu Gly Ser His His His His His His
        435                 440
```

<210> SEQ ID NO 20
<211> LENGTH: 443
<212> TYPE: PRT
<213> ORGANISM: Unknown
<220> FEATURE:
<223> OTHER INFORMATION: basf-yaad-Xa-dewA-his

<400> SEQUENCE: 20

| | | | | | | | | | | | | | | |
|---|---|---|---|---|---|---|---|---|---|---|---|---|---|---|
| Met | Ala | Gln | Thr | Gly | Thr | Glu | Arg | Val | Lys | Arg | Gly | Met | Ala | Glu | Met |
| 1 | | | | 5 | | | | | 10 | | | | | 15 | |
| Gln | Lys | Gly | Gly | Val | Ile | Met | Asp | Val | Ile | Asn | Ala | Glu | Gln | Ala | Lys |
| | | | 20 | | | | 25 | | | | | 30 | | | |
| Ile | Ala | Glu | Glu | Ala | Gly | Ala | Val | Ala | Val | Met | Ala | Leu | Glu | Arg | Val |
| | | | 35 | | | | 40 | | | | 45 | | | | |
| Pro | Ala | Asp | Ile | Arg | Ala | Ala | Gly | Gly | Val | Ala | Arg | Met | Ala | Asp | Pro |
| | 50 | | | | | 55 | | | | | 60 | | | | |
| Thr | Ile | Val | Glu | Glu | Val | Met | Asn | Ala | Val | Ser | Ile | Pro | Val | Met | Ala |
| 65 | | | | | 70 | | | | | 75 | | | | | 80 |
| Lys | Ala | Arg | Ile | Gly | His | Ile | Val | Glu | Ala | Arg | Val | Leu | Glu | Ala | Met |
| | | | | 85 | | | | | 90 | | | | | 95 | |
| Gly | Val | Asp | Tyr | Ile | Asp | Glu | Ser | Glu | Val | Leu | Thr | Pro | Ala | Asp | Glu |
| | | | | 100 | | | | | 105 | | | | | 110 | |
| Glu | Phe | His | Leu | Asn | Lys | Asn | Glu | Tyr | Thr | Val | Pro | Phe | Val | Cys | Gly |
| | | | 115 | | | | | 120 | | | | | 125 | | |
| Cys | Arg | Asp | Leu | Gly | Glu | Ala | Thr | Arg | Arg | Ile | Ala | Glu | Gly | Ala | Ser |
| | 130 | | | | | 135 | | | | | 140 | | | | |
| Met | Leu | Arg | Thr | Lys | Gly | Glu | Pro | Gly | Thr | Gly | Asn | Ile | Val | Glu | Ala |
| 145 | | | | | 150 | | | | | 155 | | | | | 160 |
| Val | Arg | His | Met | Arg | Lys | Val | Asn | Ala | Gln | Val | Arg | Lys | Val | Val | Ala |
| | | | | 165 | | | | | 170 | | | | | 175 | |
| Met | Ser | Glu | Asp | Glu | Leu | Met | Thr | Glu | Ala | Lys | Asn | Leu | Gly | Ala | Pro |
| | | | 180 | | | | | 185 | | | | | 190 | | |
| Tyr | Glu | Leu | Leu | Leu | Gln | Ile | Lys | Lys | Asp | Gly | Lys | Leu | Pro | Val | Val |
| | | | | 195 | | | | | 200 | | | | | 205 | |
| Asn | Phe | Ala | Ala | Gly | Gly | Val | Ala | Thr | Pro | Ala | Asp | Ala | Ala | Leu | Met |
| | | 210 | | | | | 215 | | | | | 220 | | | |
| Met | Gln | Leu | Gly | Ala | Asp | Gly | Val | Phe | Val | Gly | Ser | Gly | Ile | Phe | Lys |
| 225 | | | | | 230 | | | | | 235 | | | | | 240 |
| Ser | Asp | Asn | Pro | Ala | Lys | Phe | Ala | Lys | Ala | Ile | Val | Glu | Ala | Thr | Thr |
| | | | | 245 | | | | | 250 | | | | | 255 | |
| His | Phe | Thr | Asp | Tyr | Lys | Leu | Ile | Ala | Glu | Leu | Ser | Lys | Glu | Leu | Gly |
| | | | 260 | | | | | 265 | | | | | 270 | | |
| Thr | Ala | Met | Lys | Gly | Ile | Glu | Ile | Ser | Asn | Leu | Leu | Pro | Glu | Gln | Arg |
| | | 275 | | | | | 280 | | | | | 285 | | | |
| Met | Gln | Glu | Arg | Gly | Trp | Arg | Ser | Ile | Glu | Gly | Arg | Met | Arg | Phe | Ile |
| | 290 | | | | | 295 | | | | | 300 | | | | |
| Val | Ser | Leu | Leu | Ala | Phe | Thr | Ala | Ala | Thr | Ala | Thr | Ala | Leu | Pro |
| 305 | | | | | 310 | | | | | 315 | | | | | 320 |
| Ala | Ser | Ala | Ala | Lys | Asn | Ala | Lys | Leu | Ala | Thr | Ser | Ala | Ala | Phe | Ala |
| | | | | 325 | | | | | 330 | | | | | 335 | |
| Lys | Gln | Ala | Glu | Gly | Thr | Thr | Cys | Asn | Val | Gly | Ser | Ile | Ala | Cys | Cys |
| | | | 340 | | | | | 345 | | | | | 350 | | |
| Asn | Ser | Pro | Ala | Glu | Thr | Asn | Asn | Asp | Ser | Leu | Leu | Ser | Gly | Leu | Leu |
| | | 355 | | | | | 360 | | | | | 365 | | | |

```
Gly Ala Gly Leu Leu Asn Gly Leu Ser Gly Asn Thr Gly Ser Ala Cys
        370                 375                 380

Ala Lys Ala Ser Leu Ile Asp Gln Leu Gly Leu Ala Leu Val Asp
385                 390                 395                 400

His Thr Glu Glu Gly Pro Val Cys Lys Asn Ile Val Ala Cys Cys Pro
                    405                 410                 415

Glu Gly Thr Thr Asn Cys Val Ala Val Asp Asn Ala Gly Ala Gly Thr
                420                 425                 430

Lys Ala Glu Gly Ser His His His His His His
            435                 440

<210> SEQ ID NO 21
<211> LENGTH: 1395
<212> TYPE: DNA
<213> ORGANISM: Unknown
<220> FEATURE:
<221> NAME/KEY: CDS
<222> LOCATION: (1)..(1395)
<223> OTHER INFORMATION: basf-yaaD-Xa-rodA-his

<400> SEQUENCE: 21 atg gct caa aca ggt act gaa cgt gta aaa cgc gga atg gca gaa atg     48
Met Ala Gln Thr Gly Thr Glu Arg Val Lys Arg Gly Met Ala Glu Met
1               5                   10                  15 caa aaa ggc ggc gtc atc atg gac gtc atc aat gcg gaa caa gcg aaa     96
Gln Lys Gly Gly Val Ile Met Asp Val Ile Asn Ala Glu Gln Ala Lys
            20                  25                  30 atc gct gaa gaa gct gga gct gtc gct gta atg gcg cta gaa cgt gtg    144
Ile Ala Glu Glu Ala Gly Ala Val Ala Val Met Ala Leu Glu Arg Val
        35                  40                  45 cca gca gat att cgc gcg gct gga gga gtt gcc cgt atg gct gac cct    192
Pro Ala Asp Ile Arg Ala Ala Gly Gly Val Ala Arg Met Ala Asp Pro
    50                  55                  60 aca atc gtg gaa gaa gta atg aat gca gta tct atc ccg gta atg gca    240
Thr Ile Val Glu Glu Val Met Asn Ala Val Ser Ile Pro Val Met Ala
65                  70                  75                  80 aaa gcg cgt atc gga cat att gtt gaa gcg cgt gtg ctt gaa gct atg    288
Lys Ala Arg Ile Gly His Ile Val Glu Ala Arg Val Leu Glu Ala Met
                85                  90                  95 ggt gtt gac tat att gat gaa agt gaa gtt ctg acg ccg gct gac gaa    336
Gly Val Asp Tyr Ile Asp Glu Ser Glu Val Leu Thr Pro Ala Asp Glu
            100                 105                 110 gaa ttt cat tta aat aaa aat gaa tac aca gtt cct ttt gtc tgt ggc    384
Glu Phe His Leu Asn Lys Asn Glu Tyr Thr Val Pro Phe Val Cys Gly
        115                 120                 125 tgc cgt gat ctt ggt gaa gca aca cgc cgt att gcg gaa ggt gct tct    432
Cys Arg Asp Leu Gly Glu Ala Thr Arg Arg Ile Ala Glu Gly Ala Ser
    130                 135                 140 atg ctt cgc aca aaa ggt gag cct gga aca ggt aat att gtt gag gct    480
Met Leu Arg Thr Lys Gly Glu Pro Gly Thr Gly Asn Ile Val Glu Ala
145                 150                 155                 160 gtt cgc cat atg cgt aaa gtt aac gct caa gtg cgc aaa gta gtt gcg    528
Val Arg His Met Arg Lys Val Asn Ala Gln Val Arg Lys Val Val Ala
                165                 170                 175 atg agt gag gat gag cta atg aca gaa gcg aaa aac cta ggt gct cct    576
Met Ser Glu Asp Glu Leu Met Thr Glu Ala Lys Asn Leu Gly Ala Pro
            180                 185                 190 tac gag ctt ctt ctt caa att aaa aaa gac ggc aag ctt cct gtc gtt    624
Tyr Glu Leu Leu Leu Gln Ile Lys Lys Asp Gly Lys Leu Pro Val Val
        195                 200                 205 aac ttt gcc gct ggc ggc gta gca act cca gct gat gct gct ctc atg    672
```

```
Asn Phe Ala Ala Gly Gly Val Ala Thr Pro Ala Asp Ala Ala Leu Met
            210                 215                 220 atg cag ctt ggt gct gac gga gta ttt gtt ggt tct ggt att ttt aaa       720
Met Gln Leu Gly Ala Asp Gly Val Phe Val Gly Ser Gly Ile Phe Lys
225                 230                 235                 240 tca gac aac cct gct aaa ttt gcg aaa gca att gtg gaa gca aca act       768
Ser Asp Asn Pro Ala Lys Phe Ala Lys Ala Ile Val Glu Ala Thr Thr
                245                 250                 255 cac ttt act gat tac aaa tta atc gct gag ttg tca aaa gag ctt ggt       816
His Phe Thr Asp Tyr Lys Leu Ile Ala Glu Leu Ser Lys Glu Leu Gly
            260                 265                 270 act gca atg aaa ggg att gaa atc tca aac tta ctt cca gaa cag cgt       864
Thr Ala Met Lys Gly Ile Glu Ile Ser Asn Leu Leu Pro Glu Gln Arg
        275                 280                 285 atg caa gaa cgc ggc tgg aga tct att gaa ggc cgc atg aag ttc tcc       912
Met Gln Glu Arg Gly Trp Arg Ser Ile Glu Gly Arg Met Lys Phe Ser
    290                 295                 300 att gct gcc gct gtc gtt gct ttc gcc gcc tcc gtc gcg gcc ctc cct       960
Ile Ala Ala Ala Val Val Ala Phe Ala Ala Ser Val Ala Ala Leu Pro
305                 310                 315                 320 cct gcc cat gat tcc cag ttc gct ggc aat ggt gtt ggc aac aag ggc      1008
Pro Ala His Asp Ser Gln Phe Ala Gly Asn Gly Val Gly Asn Lys Gly
                325                 330                 335 aac agc aac gtc aag ttc cct gtc ccc gaa aac gtg acc gtc aag cag      1056
Asn Ser Asn Val Lys Phe Pro Val Pro Glu Asn Val Thr Val Lys Gln
            340                 345                 350 gcc tcc gac aag tgc ggt gac cag gcc cag ctc tct tgc tgc aac aag      1104
Ala Ser Asp Lys Cys Gly Asp Gln Ala Gln Leu Ser Cys Cys Asn Lys
        355                 360                 365 gcc acg tac gcc ggt gac acc aca acc gtt gat gag ggt ctt ctg tct      1152
Ala Thr Tyr Ala Gly Asp Thr Thr Thr Val Asp Glu Gly Leu Leu Ser
    370                 375                 380 ggt gcc ctc agc ggc ctc atc ggc gcc ggg tct ggt gcc gaa ggt ctt      1200
Gly Ala Leu Ser Gly Leu Ile Gly Ala Gly Ser Gly Ala Glu Gly Leu
385                 390                 395                 400 ggt ctc ttc gat cag tgc tcc aag ctt gat gtt gct gtc ctc att ggc      1248
Gly Leu Phe Asp Gln Cys Ser Lys Leu Asp Val Ala Val Leu Ile Gly
                405                 410                 415 atc caa gat ctt gtc aac cag aag tgc aag caa aac att gcc tgc tgc      1296
Ile Gln Asp Leu Val Asn Gln Lys Cys Lys Gln Asn Ile Ala Cys Cys
            420                 425                 430 cag aac tcc ccc tcc agc gcg gat ggc aac ctt att ggt gtc ggt ctc      1344
Gln Asn Ser Pro Ser Ser Ala Asp Gly Asn Leu Ile Gly Val Gly Leu
        435                 440                 445 cct tgc gtt gcc ctt ggc tcc atc ctc gga tct cat cac cat cac cat      1392
Pro Cys Val Ala Leu Gly Ser Ile Leu Gly Ser His His His His His
    450                 455                 460 cac                                                                    1395
His
465

<210> SEQ ID NO 22
<211> LENGTH: 465
<212> TYPE: PRT
<213> ORGANISM: Unknown
<220> FEATURE:
<223> OTHER INFORMATION: basf-yaaD-Xa-rodA-his

<400> SEQUENCE: 22

Met Ala Gln Thr Gly Thr Glu Arg Val Lys Arg Gly Met Ala Glu Met
1               5                   10                  15
```

```
Gln Lys Gly Gly Val Ile Met Asp Val Ile Asn Ala Glu Gln Ala Lys
                20                  25                  30
Ile Ala Glu Glu Ala Gly Ala Val Ala Met Ala Leu Glu Arg Val
        35                  40                  45
Pro Ala Asp Ile Arg Ala Ala Gly Gly Val Ala Arg Met Ala Asp Pro
 50                  55                  60
Thr Ile Val Glu Glu Val Met Asn Ala Val Ser Ile Pro Val Met Ala
 65                  70                  75                  80
Lys Ala Arg Ile Gly His Ile Val Glu Ala Arg Val Leu Glu Ala Met
                85                  90                  95
Gly Val Asp Tyr Ile Asp Glu Ser Glu Val Leu Thr Pro Ala Asp Glu
                100                 105                 110
Glu Phe His Leu Asn Lys Asn Glu Tyr Thr Val Pro Phe Val Cys Gly
        115                 120                 125
Cys Arg Asp Leu Gly Glu Ala Thr Arg Arg Ile Ala Glu Gly Ala Ser
130                 135                 140
Met Leu Arg Thr Lys Gly Glu Pro Gly Thr Gly Asn Ile Val Glu Ala
145                 150                 155                 160
Val Arg His Met Arg Lys Val Asn Ala Gln Val Arg Lys Val Val Ala
                165                 170                 175
Met Ser Glu Asp Glu Leu Met Thr Glu Ala Lys Asn Leu Gly Ala Pro
        180                 185                 190
Tyr Glu Leu Leu Leu Gln Ile Lys Lys Asp Gly Lys Leu Pro Val Val
        195                 200                 205
Asn Phe Ala Ala Gly Gly Val Ala Thr Pro Ala Asp Ala Ala Leu Met
210                 215                 220
Met Gln Leu Gly Ala Asp Gly Val Phe Val Gly Ser Gly Ile Phe Lys
225                 230                 235                 240
Ser Asp Asn Pro Ala Lys Phe Ala Lys Ala Ile Val Glu Ala Thr Thr
                245                 250                 255
His Phe Thr Asp Tyr Lys Leu Ile Ala Glu Leu Ser Lys Glu Leu Gly
        260                 265                 270
Thr Ala Met Lys Gly Ile Glu Ile Ser Asn Leu Leu Pro Glu Gln Arg
        275                 280                 285
Met Gln Glu Arg Gly Trp Arg Ser Ile Glu Gly Arg Met Lys Phe Ser
290                 295                 300
Ile Ala Ala Ala Val Val Ala Phe Ala Ala Ser Val Ala Ala Leu Pro
305                 310                 315                 320
Pro Ala His Asp Ser Gln Phe Ala Gly Asn Gly Val Gly Asn Lys Gly
                325                 330                 335
Asn Ser Asn Val Lys Phe Pro Val Pro Glu Asn Val Thr Val Lys Gln
        340                 345                 350
Ala Ser Asp Lys Cys Gly Asp Gln Ala Gln Leu Ser Cys Cys Asn Lys
        355                 360                 365
Ala Thr Tyr Ala Gly Asp Thr Thr Val Asp Glu Gly Leu Leu Ser
370                 375                 380
Gly Ala Leu Ser Gly Leu Ile Gly Ala Gly Ser Gly Ala Glu Gly Leu
385                 390                 395                 400
Gly Leu Phe Asp Gln Cys Ser Lys Leu Asp Val Ala Val Leu Ile Gly
                405                 410                 415
Ile Gln Asp Leu Val Asn Gln Lys Cys Lys Gln Asn Ile Ala Cys Cys
        420                 425                 430
Gln Asn Ser Pro Ser Ser Ala Asp Gly Asn Leu Ile Gly Val Gly Leu
        435                 440                 445
```

```
Pro Cys Val Ala Leu Gly Ser Ile Leu Gly Ser His His His His
    450                 455                 460
His
465

<210> SEQ ID NO 23
<211> LENGTH: 1407
<212> TYPE: DNA
<213> ORGANISM: Unknown
<220> FEATURE:
<221> NAME/KEY: CDS
<222> LOCATION: (1)..(1407)
<223> OTHER INFORMATION: basf-yaad-Xa-BASF1-his

<400> SEQUENCE: 23 atg gct caa aca ggt act gaa cgt gta aaa cgc gga atg gca gaa atg      48
Met Ala Gln Thr Gly Thr Glu Arg Val Lys Arg Gly Met Ala Glu Met
1               5                   10                  15 caa aaa ggc ggc gtc atc atg gac gtc atc aat gcg gaa caa gcg aaa      96
Gln Lys Gly Gly Val Ile Met Asp Val Ile Asn Ala Glu Gln Ala Lys
            20                  25                  30 atc gct gaa gaa gct gga gct gtc gct gta atg gcg cta gaa cgt gtg     144
Ile Ala Glu Glu Ala Gly Ala Val Ala Val Met Ala Leu Glu Arg Val
        35                  40                  45 cca gca gat att cgc gcg gct gga gga gtt gcc cgt atg gct gac cct     192
Pro Ala Asp Ile Arg Ala Ala Gly Gly Val Ala Arg Met Ala Asp Pro
    50                  55                  60 aca atc gtg gaa gaa gta atg aat gca gta tct atc ccg gta atg gca     240
Thr Ile Val Glu Glu Val Met Asn Ala Val Ser Ile Pro Val Met Ala
65                  70                  75                  80 aaa gcg cgt atc gga cat att gtt gaa gcg cgt gtg ctt gaa gct atg     288
Lys Ala Arg Ile Gly His Ile Val Glu Ala Arg Val Leu Glu Ala Met
                85                  90                  95 ggt gtt gac tat att gat gaa agt gaa gtt ctg acg ccg gct gac gaa     336
Gly Val Asp Tyr Ile Asp Glu Ser Glu Val Leu Thr Pro Ala Asp Glu
            100                 105                 110 gaa ttt cat tta aat aaa aat gaa tac aca gtt cct ttt gtc tgt ggc     384
Glu Phe His Leu Asn Lys Asn Glu Tyr Thr Val Pro Phe Val Cys Gly
        115                 120                 125 tgc cgt gat ctt ggt gaa gca aca cgc cgt att gcg gaa ggt gct tct     432
Cys Arg Asp Leu Gly Glu Ala Thr Arg Arg Ile Ala Glu Gly Ala Ser
    130                 135                 140 atg ctt cgc aca aaa ggt gag cct gga aca ggt aat att gtt gag gct     480
Met Leu Arg Thr Lys Gly Glu Pro Gly Thr Gly Asn Ile Val Glu Ala
145                 150                 155                 160 gtt cgc cat atg cgt aaa gtt aac gct caa gtg cgc aaa gta gtt gcg     528
Val Arg His Met Arg Lys Val Asn Ala Gln Val Arg Lys Val Val Ala
                165                 170                 175 atg agt gag gat gag cta atg aca gaa gcg aaa aac cta ggt gct cct     576
Met Ser Glu Asp Glu Leu Met Thr Glu Ala Lys Asn Leu Gly Ala Pro
            180                 185                 190 tac gag ctt ctt ctt caa att aaa aaa gac ggc aag ctt cct gtc gtt     624
Tyr Glu Leu Leu Leu Gln Ile Lys Lys Asp Gly Lys Leu Pro Val Val
        195                 200                 205 aac ttt gcc gct ggc ggc gta gca act cca gct gat gct gct ctc atg     672
Asn Phe Ala Ala Gly Gly Val Ala Thr Pro Ala Asp Ala Ala Leu Met
    210                 215                 220 atg cag ctt ggt gct gac gga gta ttt gtt ggt tct ggt att ttt aaa     720
Met Gln Leu Gly Ala Asp Gly Val Phe Val Gly Ser Gly Ile Phe Lys
225                 230                 235                 240 tca gac aac cct gct aaa ttt gcg aaa gca att gtg gaa gca aca act     768
```

```
Ser Asp Asn Pro Ala Lys Phe Ala Lys Ala Ile Val Glu Ala Thr Thr
            245                 250                 255 cac ttt act gat tac aaa tta atc gct gag ttg tca aaa gag ctt ggt      816
His Phe Thr Asp Tyr Lys Leu Ile Ala Glu Leu Ser Lys Glu Leu Gly
        260                 265                 270 act gca atg aaa ggg att gaa atc tca aac tta ctt cca gaa cag cgt      864
Thr Ala Met Lys Gly Ile Glu Ile Ser Asn Leu Leu Pro Glu Gln Arg
            275                 280                 285 atg caa gaa cgc ggc tgg aga tct att gaa ggc cgc atg aag ttc tcc      912
Met Gln Glu Arg Gly Trp Arg Ser Ile Glu Gly Arg Met Lys Phe Ser
        290                 295                 300 gtc tcc gcc gcc gtc ctc gcc ttc gcc gcc tcc gtc gcc gcc ctc cct      960
Val Ser Ala Ala Val Leu Ala Phe Ala Ala Ser Val Ala Ala Leu Pro
305                 310                 315                 320 cag cac gac tcc gcc gcc ggc aac ggc aac ggc gtc ggc aac aag ttc     1008
Gln His Asp Ser Ala Ala Gly Asn Gly Asn Gly Val Gly Asn Lys Phe
                325                 330                 335 cct gtc cct gac gac gtc acc gtc aag cag gcc acc gac aag tgc ggc     1056
Pro Val Pro Asp Asp Val Thr Val Lys Gln Ala Thr Asp Lys Cys Gly
            340                 345                 350 gac cag gcc cag ctc tcc tgc tgc aac aag gcc acc tac gcc ggc gac     1104
Asp Gln Ala Gln Leu Ser Cys Cys Asn Lys Ala Thr Tyr Ala Gly Asp
        355                 360                 365 gtc ctc acc gac atc gac gag ggc atc ctc gcc ggc ctc ctc aag aac     1152
Val Leu Thr Asp Ile Asp Glu Gly Ile Leu Ala Gly Leu Leu Lys Asn
    370                 375                 380 ctc atc ggc ggc ggc tcc ggc tcc gag ggc ctc ggc ctc ttc gac cag     1200
Leu Ile Gly Gly Gly Ser Gly Ser Glu Gly Leu Gly Leu Phe Asp Gln
385                 390                 395                 400 tgc gtc aag ctc gac ctc cag atc tcc gtc atc ggc atc cct atc cag     1248
Cys Val Lys Leu Asp Leu Gln Ile Ser Val Ile Gly Ile Pro Ile Gln
                405                 410                 415 gac ctc ctc aac cag gtc aac aag cag tgc aag cag aac atc gcc tgc     1296
Asp Leu Leu Asn Gln Val Asn Lys Gln Cys Lys Gln Asn Ile Ala Cys
            420                 425                 430 tgc cag aac tcc cct tcc gac gcc acc ggc tcc ctc gtc aac ctc ggc     1344
Cys Gln Asn Ser Pro Ser Asp Ala Thr Gly Ser Leu Val Asn Leu Gly
        435                 440                 445 ctc ggc aac cct tgc atc cct gtc tcc ctc ctc cat atg gga tct cat     1392
Leu Gly Asn Pro Cys Ile Pro Val Ser Leu Leu His Met Gly Ser His
    450                 455                 460 cac cat cac cat cac                                                  1407
His His His His His
465

<210> SEQ ID NO 24
<211> LENGTH: 469
<212> TYPE: PRT
<213> ORGANISM: Unknown
<220> FEATURE:
<223> OTHER INFORMATION: basf-yaad-Xa-BASF1-his

<400> SEQUENCE: 24

Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60
```

```
Thr Ile Val Glu Glu Val Met Asn Ala Val Ser Ile Pro Val Met Ala
 65                  70                  75                  80

Lys Ala Arg Ile Gly His Ile Val Glu Ala Arg Val Leu Glu Ala Met
                 85                  90                  95

Gly Val Asp Tyr Ile Asp Glu Ser Glu Val Leu Thr Pro Ala Asp Glu
                100                 105                 110

Glu Phe His Leu Asn Lys Asn Glu Tyr Thr Val Pro Phe Val Cys Gly
            115                 120                 125

Cys Arg Asp Leu Gly Glu Ala Thr Arg Arg Ile Ala Glu Gly Ala Ser
        130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
                180                 185                 190

Tyr Glu Leu Leu Leu Gln Ile Lys Lys Asp Gly Lys Leu Pro Val Val
            195                 200                 205

Asn Phe Ala Ala Gly Gly Val Ala Thr Pro Ala Asp Ala Ala Leu Met
        210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
                260                 265                 270

Thr Ala Met Lys Gly Ile Glu Ile Ser Asn Leu Leu Pro Glu Gln Arg
            275                 280                 285

Met Gln Glu Arg Gly Trp Arg Ser Ile Glu Gly Arg Met Lys Phe Ser
        290                 295                 300

Val Ser Ala Ala Val Leu Ala Phe Ala Ala Ser Val Ala Ala Leu Pro
305                 310                 315                 320

Gln His Asp Ser Ala Ala Gly Asn Gly Asn Gly Val Gly Asn Lys Phe
                325                 330                 335

Pro Val Pro Asp Asp Val Thr Val Lys Gln Ala Thr Asp Lys Cys Gly
                340                 345                 350

Asp Gln Ala Gln Leu Ser Cys Cys Asn Lys Ala Thr Tyr Ala Gly Asp
            355                 360                 365

Val Leu Thr Asp Ile Asp Glu Gly Ile Leu Ala Gly Leu Leu Lys Asn
        370                 375                 380

Leu Ile Gly Gly Gly Ser Gly Ser Glu Gly Leu Gly Leu Phe Asp Gln
385                 390                 395                 400

Cys Val Lys Leu Asp Leu Gln Ile Ser Val Ile Gly Ile Pro Ile Gln
                405                 410                 415

Asp Leu Leu Asn Gln Val Asn Lys Gln Cys Lys Gln Asn Ile Ala Cys
                420                 425                 430

Cys Gln Asn Ser Pro Ser Asp Ala Thr Gly Ser Leu Val Asn Leu Gly
            435                 440                 445

Leu Gly Asn Pro Cys Ile Pro Val Ser Leu Leu His Met Gly Ser His
        450                 455                 460

His His His His His
465
```

```
<210> SEQ ID NO 25
<211> LENGTH: 28
<212> TYPE: DNA
<213> ORGANISM: Unknown
<220> FEATURE:
<223> OTHER INFORMATION: Hal570 oligonucleotide

<400> SEQUENCE: 25
gcgcgcccat ggctcaaaca ggtactga                                    28

<210> SEQ ID NO 26
<211> LENGTH: 28
<212> TYPE: DNA
<213> ORGANISM: Unknown
<220> FEATURE:
<223> OTHER INFORMATION: Hal571 oligonucleotide

<400> SEQUENCE: 26
gcagatctcc agccgcgttc ttgcatac                                    28

<210> SEQ ID NO 27
<211> LENGTH: 30
<212> TYPE: DNA
<213> ORGANISM: Unknown
<220> FEATURE:
<223> OTHER INFORMATION: Hal572 oligonucleotide

<400> SEQUENCE: 27
ggccatggga ttaacaatag gtgtactagg                                  30

<210> SEQ ID NO 28
<211> LENGTH: 33
<212> TYPE: DNA
<213> ORGANISM: Unknown
<220> FEATURE:
<223> OTHER INFORMATION: Hal573 oligonucleotide

<400> SEQUENCE: 28
gcagatctta caagtgcctt ttgcttatat tcc                              33

<210> SEQ ID NO 29
<211> LENGTH: 20
<212> TYPE: DNA
<213> ORGANISM: Artificial
<220> FEATURE:
<223> OTHER INFORMATION: Primer 1 20-mer

<400> SEQUENCE: 29
aattaaccat ggctcaaaca                                             20

<210> SEQ ID NO 30
<211> LENGTH: 74
<212> TYPE: DNA
<213> ORGANISM: Artificial
<220> FEATURE:
<223> OTHER INFORMATION: Primer 2 74-mer

<400> SEQUENCE: 30
gccatatttt ttaataatat gaataatttt acgggtaata cgacgcaggt ttttgcagca 60
agcgatcgag ccga                                                   74

<210> SEQ ID NO 31
<211> LENGTH: 40
<212> TYPE: DNA
<213> ORGANISM: Artificial
<220> FEATURE:
<223> OTHER INFORMATION: Primer 3 40-mer
```

<400> SEQUENCE: 31
atattattaa aaaatatggc aactcccccg ctgagaccaa                                40

<210> SEQ ID NO 32
<211> LENGTH: 21
<212> TYPE: DNA
<213> ORGANISM: Artificial
<220> FEATURE:
<223> OTHER INFORMATION: Primer 4 21-mer

<400> SEQUENCE: 32
ctaattaagc ttagtgatgg t                                                   21

<210> SEQ ID NO 33
<211> LENGTH: 74
<212> TYPE: DNA
<213> ORGANISM: Artificial
<220> FEATURE:
<223> OTHER INFORMATION: Primer 5 74-mer

<400> SEQUENCE: 33
gccatatttt ttaataatat gaatgccttt acgaataata cgacgcaggt ttttgcagca         60
agcgatcgag ccga                                                           74

<210> SEQ ID NO 34
<211> LENGTH: 40
<212> TYPE: DNA
<213> ORGANISM: Artificial
<220> FEATURE:
<223> OTHER INFORMATION: Primer 6 40-mer

<400> SEQUENCE: 34
atattattaa aaaatatggc aactcccccg ctgagaccaa                                40

<210> SEQ ID NO 35
<211> LENGTH: 38
<212> TYPE: DNA
<213> ORGANISM: Unknown
<220> FEATURE:
<223> OTHER INFORMATION: KaM416 oligonucleotide

<400> SEQUENCE: 35
gcagcccatc agggatccct cagccttggt accagcgc                                 38

<210> SEQ ID NO 36
<211> LENGTH: 50
<212> TYPE: DNA
<213> ORGANISM: Unknown
<220> FEATURE:
<223> OTHER INFORMATION: KaM417 oligonucleotide

<400> SEQUENCE: 36
cccgtagcta gtggatccat tgaaggccgc atgaagttct ccgtctccgc                    50

<210> SEQ ID NO 37
<211> LENGTH: 45
<212> TYPE: DNA
<213> ORGANISM: Unknown
<220> FEATURE:
<223> OTHER INFORMATION: KaM434 oligonucleotide

<400> SEQUENCE: 37
gctaagcgga tccattgaag gccgcatgaa gttctccatt gctgc                         45

```
<210> SEQ ID NO 38
<211> LENGTH: 30
<212> TYPE: DNA
<213> ORGANISM: Unknown
<220> FEATURE:
<223> OTHER INFORMATION: KaM435 oligonucleotide

<400> SEQUENCE: 38
ccaatgggga tccgaggatg gagccaaggg                                             30

<210> SEQ ID NO 39
<211> LENGTH: 38
<212> TYPE: DNA
<213> ORGANISM: Unknown
<220> FEATURE:
<223> OTHER INFORMATION: KaM418 oligonucleotide

<400> SEQUENCE: 39
ctgccattca ggggatccca tatggaggag ggagacag                                    38

<210> SEQ ID NO 40
<211> LENGTH: 32
<212> TYPE: DNA
<213> ORGANISM: Unknown
<220> FEATURE:
<223> OTHER INFORMATION: KaM464 oligonucleotide

<400> SEQUENCE: 40
cgttaaggat ccgaggatgt tgatgggggt gc                                          32

<210> SEQ ID NO 41
<211> LENGTH: 35
<212> TYPE: DNA
<213> ORGANISM: Unknown
<220> FEATURE:
<223> OTHER INFORMATION: KaM465 oligonucleotide

<400> SEQUENCE: 41
gctaacagat ctatgttcgc ccgtctcccc gtcgt                                       35

<210> SEQ ID NO 42
<211> LENGTH: 461
<212> TYPE: PRT
<213> ORGANISM: Artificial
<220> FEATURE:
<223> OTHER INFORMATION: YaaD-DewA Cys3-T7-DewA 6His

<400> SEQUENCE: 42
```

Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60

Thr Ile Val Glu Glu Val Met Asn Ala Val Ser Ile Pro Val Met Ala
65                  70                  75                  80

Lys Ala Arg Ile Gly His Ile Val Glu Ala Arg Val Leu Glu Ala Met
                85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
                195                 200                 205

Asn Phe Ala Ala Gly Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
        275                 280                 285

Met Gln Glu Arg Gly Trp Arg Ser Ile Glu Gly Arg Met Arg Phe Ile
    290                 295                 300

Val Ser Leu Leu Ala Phe Thr Ala Ala Thr Ala Thr Ala Leu Pro
305                 310                 315                 320

Ala Ser Ala Ala Lys Asn Ala Lys Leu Ala Thr Ser Ala Ala Phe Ala
                325                 330                 335

Lys Gln Ala Glu Gly Thr Thr Cys Asn Val Gly Ser Ile Ala Cys Cys
            340                 345                 350

Lys Asn Leu Arg Arg Ile Thr Arg Lys Ile Ile His Ile Ile Lys Lys
        355                 360                 365

Tyr Gly Asn Ser Pro Ala Glu Thr Asn Asn Asp Ser Leu Leu Ser Gly
    370                 375                 380

Leu Leu Gly Ala Gly Leu Leu Asn Gly Leu Ser Gly Asn Thr Gly Ser
385                 390                 395                 400

Ala Cys Ala Lys Ala Ser Leu Ile Asp Gln Leu Gly Leu Leu Ala Leu
                405                 410                 415

Val Asp His Thr Glu Glu Gly Pro Val Cys Lys Asn Ile Val Ala Cys
            420                 425                 430

Cys Pro Glu Gly Thr Thr Asn Cys Val Ala Val Asp Asn Ala Gly Ala
        435                 440                 445

Gly Thr Lys Ala Glu Gly Ser His His His His His
    450                 455                 460

<210> SEQ ID NO 43
<211> LENGTH: 461
<212> TYPE: PRT
<213> ORGANISM: Artificial
<220> FEATURE:
<223> OTHER INFORMATION: YaaD-DewA Cys3-G10-DewA 6His

<400> SEQUENCE: 43

Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

```
Ile Ala Glu Glu Ala Gly Ala Val Ala Val Met Ala Leu Glu Arg Val
             35                  40                  45

Pro Ala Asp Ile Arg Ala Ala Gly Gly Val Ala Arg Met Ala Asp Pro
 50                  55                  60

Thr Ile Val Glu Glu Val Met Asn Ala Val Ser Ile Pro Val Met Ala
 65                  70                  75                  80

Lys Ala Arg Ile Gly His Ile Val Glu Ala Arg Val Leu Glu Ala Met
                 85                  90                  95

Gly Val Asp Tyr Ile Asp Glu Ser Glu Val Leu Thr Pro Ala Asp Glu
                100                 105                 110

Glu Phe His Leu Asn Lys Asn Glu Tyr Thr Val Pro Phe Val Cys Gly
            115                 120                 125

Cys Arg Asp Leu Gly Glu Ala Thr Arg Arg Ile Ala Glu Gly Ala Ser
130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
            195                 200                 205

Asn Phe Ala Ala Gly Gly Val Ala Thr Pro Ala Asp Ala Ala Leu Met
210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
            275                 280                 285

Met Gln Glu Arg Gly Trp Arg Ser Ile Glu Gly Arg Met Arg Phe Ile
290                 295                 300

Val Ser Leu Leu Ala Phe Thr Ala Ala Thr Ala Thr Ala Leu Pro
305                 310                 315                 320

Ala Ser Ala Ala Lys Asn Ala Lys Leu Ala Thr Ser Ala Ala Phe Ala
                325                 330                 335

Lys Gln Ala Glu Gly Thr Thr Cys Asn Val Gly Ser Ile Ala Cys Cys
            340                 345                 350

Lys Asn Leu Arg Arg Ile Ile Arg Lys Gly Ile His Ile Ile Lys Lys
            355                 360                 365

Tyr Gly Asn Ser Pro Ala Glu Thr Asn Asn Asp Ser Leu Leu Ser Gly
370                 375                 380

Leu Leu Gly Ala Gly Leu Leu Asn Gly Leu Ser Gly Asn Thr Gly Ser
385                 390                 395                 400

Ala Cys Ala Lys Ala Ser Leu Ile Asp Gln Leu Gly Leu Leu Ala Leu
                405                 410                 415

Val Asp His Thr Glu Glu Gly Pro Val Cys Lys Asn Ile Val Ala Cys
            420                 425                 430
```

```
Cys Pro Glu Gly Thr Thr Asn Cys Val Ala Val Asp Asn Ala Gly Ala
            435                 440                 445
Gly Thr Lys Ala Glu Gly Ser His His His His His His
    450                 455                 460
```